United States Patent
Uber, III et al.

(10) Patent No.: US 9,925,331 B2
(45) Date of Patent: Mar. 27, 2018

(54) DOUBLE ACTION INFUSION SYSTEM

(71) Applicant: Boston Scientific Limited, Hamilton (BM)

(72) Inventors: Arthur E. Uber, III, Pittsburgh, PA (US); Michael J. Bonnette, Minneapolis, MN (US)

(73) Assignee: Boston Scientific Limited, Hamilton (BM)

( * ) Notice: Subject to any disclaimer, the term of this patent is extended or adjusted under 35 U.S.C. 154(b) by 535 days.

(21) Appl. No.: 14/471,328

(22) Filed: Aug. 28, 2014

(65) Prior Publication Data

US 2015/0051487 A1 Feb. 19, 2015

Related U.S. Application Data

(63) Continuation-in-part of application No. 13/794,528, filed on Mar. 11, 2013, now Pat. No. 9,107,986.

(51) Int. Cl.
*A61M 5/142* (2006.01)
*A61M 5/00* (2006.01)

(52) U.S. Cl.
CPC .......... *A61M 5/1422* (2013.01); *A61M 5/007* (2013.01); *A61M 2206/22* (2013.01)

(58) Field of Classification Search
CPC .... A61M 5/14; A61M 2206/22; A61M 5/007; A61M 5/14216; A61M 5/1422;
(Continued)

(56) References Cited

U.S. PATENT DOCUMENTS 4,715,959 A * 12/1987 Allan ................ A61M 1/16
210/321.71
4,902,276 A 2/1990 Zakko
(Continued)

FOREIGN PATENT DOCUMENTS

DE 202011108638 3/2013
DE 102011120105 A1 6/2013
(Continued)

OTHER PUBLICATIONS

"Application Serial No. PCT/US15/47240, Invitation to Pay Additional Fees and Partial Search Report dated Dec. 3, 2015", 7 pgs.
(Continued)

*Primary Examiner* — Andrew Gilbert
*Assistant Examiner* — Hamza Darb
(74) *Attorney, Agent, or Firm* — Schwegman Lundberg & Woessner, P.A.

(57) ABSTRACT

An infusion system includes a double action infusion pump. The pump includes a cylinder and a reciprocating piston received within the cylinder, the reciprocating piston separating a first pump chamber from a second pump chamber of the cylinder. A reciprocating motor is coupled with the reciprocating piston, and the first and second pump chambers alternate between filling and evacuating conditions with reciprocation of the reciprocating piston through operation of the reciprocating motor, and the speed of reciprocation is varied to provide a continuous output of fluid between the first and second pump chambers. A fluid source and a catheter are optionally coupled with the double action infusion pump. The catheter includes one or more infusion ports near a catheter distal portion, and the one or more infusion ports receive and expel the continuous output of fluid from the double action infusion pump.

19 Claims, 12 Drawing Sheets

(58) Field of Classification Search
CPC .............. A61M 5/1412; A61M 5/1456; A61M 2205/106; A61M 1/30; A61M 2005/1403; A61M 5/3146; A61M 2005/1402
See application file for complete search history.

(56) References Cited

U.S. PATENT DOCUMENTS

| | | | |
|---|---|---|---|
| 5,916,197 | A | 6/1999 | Reilly et al. |
| 5,968,015 | A * | 10/1999 | Yamamoto ........ A61M 5/14546 128/DIG. 1 |
| 6,158,967 | A | 12/2000 | Dupre |
| 6,197,000 | B1 | 3/2001 | Reilly et al. |
| 7,842,010 | B2 | 11/2010 | Bonnette et al. |
| 7,935,077 | B2 | 5/2011 | Thor et al. |
| 2001/0051785 | A1 | 12/2001 | Bonnette et al. |
| 2008/0275393 | A1 | 11/2008 | Bonnette et al. |
| 2011/0152681 | A1 | 6/2011 | Reilly |
| 2011/0300010 | A1 | 12/2011 | Jarnagin et al. |
| 2012/0076666 | A1 * | 3/2012 | Romain .................. F04B 5/02 417/42 |
| 2012/0244018 | A1 | 9/2012 | Reilly |
| 2014/0249412 | A1 * | 9/2014 | Yamamoto ............ A61M 5/145 600/432 |

FOREIGN PATENT DOCUMENTS

| | | |
|---|---|---|
| EP | 2735376 A1 | 5/2014 |
| WO | WO-99/21598 A1 | 5/1999 |
| WO | WO-2016/033351 A2 | 3/2016 |

OTHER PUBLICATIONS

"International Application Serial No. PCT/US15/47240, International Search Report dated Mar. 9, 2016", 6 pgs.
"International Application Serial No. PCT/US15/47240, Written Opinion dated Mar. 9, 2016", 11 pgs.
The International Search Report and Written Opinion dated Jun. 10, 2014 from corresponding PCT Application No. PCT/US2014/020321 filed on Mar. 4, 2014.

* cited by examiner

DOUBLE ACTION INFUSION SYSTEM

CROSS-REFERENCE TO RELATED PATENT DOCUMENTS

This patent application is a continuation-in-part of U.S. patent application Ser. No. 13/794,528, filed on Mar. 11, 2013,mand now a patent U.S. Pat. No. 9,107,986, which application is incorporated herein by reference in its entirety.

TECHNICAL FIELD

This document pertains generally, but not by way of limitation, to infusion and contrast delivery systems.

BACKGROUND

Thrombectomy is a procedure for removing thrombus from the vasculature. Mechanical and fluid based systems are used to remove thrombus and accordingly open clogged or partially clogged vessels. With fluid based systems an infusion fluid including one or more of saline, lytics and the like is infused to a treatment area of a vessel with a catheter, for instance a thrombectomy catheter. The hydrodynamic force of the infusion fluid and optionally the characteristics of the lytics dislodge thrombus and accordingly open the vessel.

In one example, the infusion fluid is delivered to the thrombectomy catheter in a pulsed manner with a pump including a single piston. The piston is moved in a first direction to draw fluid into a cylinder, and then moved in a second direction to push the fluid out of the cylinder to a treatment feature of the thrombectomy catheter (e.g., an orifice). The pulses of fluid generated by the piston pump are then discontinuously applied through the treatment feature of the thrombectomy catheter to dislodge thrombus from the vessel wall. Optionally, the cylinder is prefilled with a fluid (e.g., contrast fluid or infusion fluid for thrombectomy) and the piston is driven in a single direction to gradually infuse the fluid. Upon full delivery of the fluid the cylinder must be refilled before operation is continued.

One example of an injection system and a pump system therein are described in U.S. Pat. No. 5,916,197. In the example pump system at least one chamber has disposed therein a pressurizing mechanism to pressurize liquid medium within the chamber. Preferably, the pressurizing mechanism positively displaces the liquid medium through generally linear motion of the pressurizing mechanism. Through reciprocating linear motion of the pressurizing mechanism (for example, a piston), the liquid medium is alternatively drawn into the chamber from a source of liquid medium (for example, a container) and forced out of the chamber under a desired pressure.

Another example of a system for delivery of a medical fluid is described in US Published Patent Application 2011/ 0152681. The system includes a pump system including a pressurizing unit to pressurize the medical fluid and a drive system in operative connection with the pressurizing unit. The pump system exhibits variation in pressure during operation. The system further includes a compensating system in fluid connection with the medical fluid pressurized by the pressurizing unit. The compensating system defines a displacement volume in fluid connection with the pressurized medical fluid that is altered in a predetermined manner to alter the variation in pressure. The compensating system can, for example, reduce pulsatility of pressure during flow.

Yet another example of a system for delivery of a medical fluid is described in US Published Patent Application 2012/ 0244018. The system includes a pump including a plurality of at least three chambers. Each of the plurality of chambers includes an inlet through which fluid is drawn into the chamber and an outlet from which fluid is expelled from the chamber. The pump system further includes a common outlet channel fluid communication with the outlet of each of the plurality of chambers and a plurality of at least three pistons. Each of the positions is slidably disposed within a respective one of the plurality of chambers. The system further includes a drive system including a cam shaft including a plurality of at least three cam lobes. The drive system further includes a plurality of at least three cam lobe followers. Each of the cam lobe followers is in operative connective with a respective one of the plurality of cam lobes and is adapted to be placed in operative connection with a respective one of the plurality of pistons. The profile of each of the plurality of cam lobes is adapted to provide a transient increase or spike in calculated theoretical output of the pump system to reduce periodic variation in measured output thereof.

In other examples, a pump with a reciprocating piston includes a drive mechanism, such as a motor, that reverses its direction to accordingly reverse the movement of the piston. The piston is accordingly decelerated and accelerated as the piston transitions from its stroke in a first direction to a second stroke in an opposed direction.

In another example a multi-cylinder pump including a plurality of corresponding pistons are coordinated to provide a continuous flow of infusion fluid. Stated another way, the plurality of pistons are operated out of sync with one another to ensure that as one of the cylinders is filling with infusion fluid another of the cylinders is providing infusion fluid output. A mechanism (e.g., a software algorithm, mechanical mechanism or the like) is used to coordinate the pistons in this manner

OVERVIEW

The present inventors have recognized, among other things, that a problem to be solved can include providing a continuous flow of infusion fluid to a vessel (e.g., for thrombus removal, contrast injection or the like) with a single reciprocating piston. Multi-piston pumps, when the pistons are coordinated, are able to provide continuous flow. However, coordinating algorithms or mechanical linkages are needed to sync the pistons and provide a continuous flow of fluid. Additionally, multi-piston pumps have a large volume to accommodate the plurality of cylinders, pistons and operating mechanisms.

In an example, the present subject matter can provide a solution to this problem, such as by a double action infusion pump using a single piston to provide fluid flow during reciprocation of the piston in first and second directions. Each of first and second pump chambers within the cylinder are alternately filled and evacuated with movement of a single piston. By varying the speed of the piston reciprocation (e.g., having different speeds in an intermediate segment of the cylinder and near top and bottom zones of the cylinder) the double action piston pump provides a continuous output of infusion fluid. The continuous output from the pump is delivered to one or more infusion ports of a catheter in one example, and the double action infusion pump thereby provides a continuous infusion flow through the infusion ports. A single piston infusion pump with this arrangement is compact relative to multi-piston pumps and readily configured for installation within a larger infusion system already configured for use of a single action reciprocating piston pump.

Furthermore, by varying a speed of the reciprocating piston from one end of an intermediate segment of the cylinder to the ends of the top or bottom zones (e.g., immediately prior to reversing movement of the piston) the continuous output of the double action pump provides (or approaches) a static flow rate, and the continuous infusion flow from the one or more infusion ports similarly provides (or approaches) a static flow rate. In one example, the speed is varied in these regions between an initial piston speed that nearly matches the piston speed within the intermediate segment and a greater terminating speed near the ends of the top and bottom zones (e.g., at the end of the piston travel).

Moreover, the inertia provided by the piston and drive mechanism during the reversing of the drive mechanism acts against a motor of a reciprocating pump in some examples, for instance during transition of movement of the piston from a first direction to a second direction. In one example, a double action infusion pump includes a drive mechanism, such as a motor, that operates (rotates) in a single direction while driving the piston in a reciprocating fashion. The piston, including a piston carriage, is reciprocated with the single direction drive mechanism with one or more reversing mechanisms including, but not limited to a ball reverser, a rolling ring drive or the like. The reversing mechanisms ensure the drive mechanism experiences minimal inertia from reciprocating movement of the piston and eliminate the inertia change due to the reversal of a motor drive mechanism. Instead, the reversing mechanisms transform the single direction movement of the drive mechanism into reciprocating movement of the piston with minimal inertia, mechanical slop or the like. In yet another example, one or more of the drive mechanism or the reversing mechanism are manipulated during operation of the double action infusion pump to correspondingly change the velocity of the piston to provide a constant flow of fluid (e.g., to a catheter or from an injector for contrast). In still another example, a combination of opposed motors or a motor and opposed bias mechanism are used to minimize the effects of inertia, mechanical slop and the like of the piston by providing a counter force that biases the piston in an opposed fashion as it transitions from movement in the first direction to the second direction.

The present inventors have recognized, among other things, that a problem to be solved can include providing a continuous flow of infusion fluid to a vessel (e.g., for thrombus removal, contrast injection or the like) with a single reciprocating piston. Multi-piston pumps, when the pistons are coordinated, are able to provide continuous flow. However, coordinating algorithms or mechanical linkages are needed to sync the pistons and provide a continuous flow of fluid. Additionally, multi-piston pumps have a large volume to accommodate the plurality of cylinders, pistons and operating mechanisms.

Further still, an infusion system including the double action infusion provides a single piston pump configured to provide a continuous uninterrupted flow of infusion fluid to a treatment site. In one example, the infusion system provided herein is used as a contrast injector. In contrast to previous systems that use a single piston containing a reservoir of contrast fluid within the cylinder, the infusion system including the double action infusion pump is able to continuously deliver contrast fluid without refilling of the pump cylinder. Instead, the contrast fluid is refilled in a reservoir (e.g., fluid source) in communication with the double action infusion pump.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
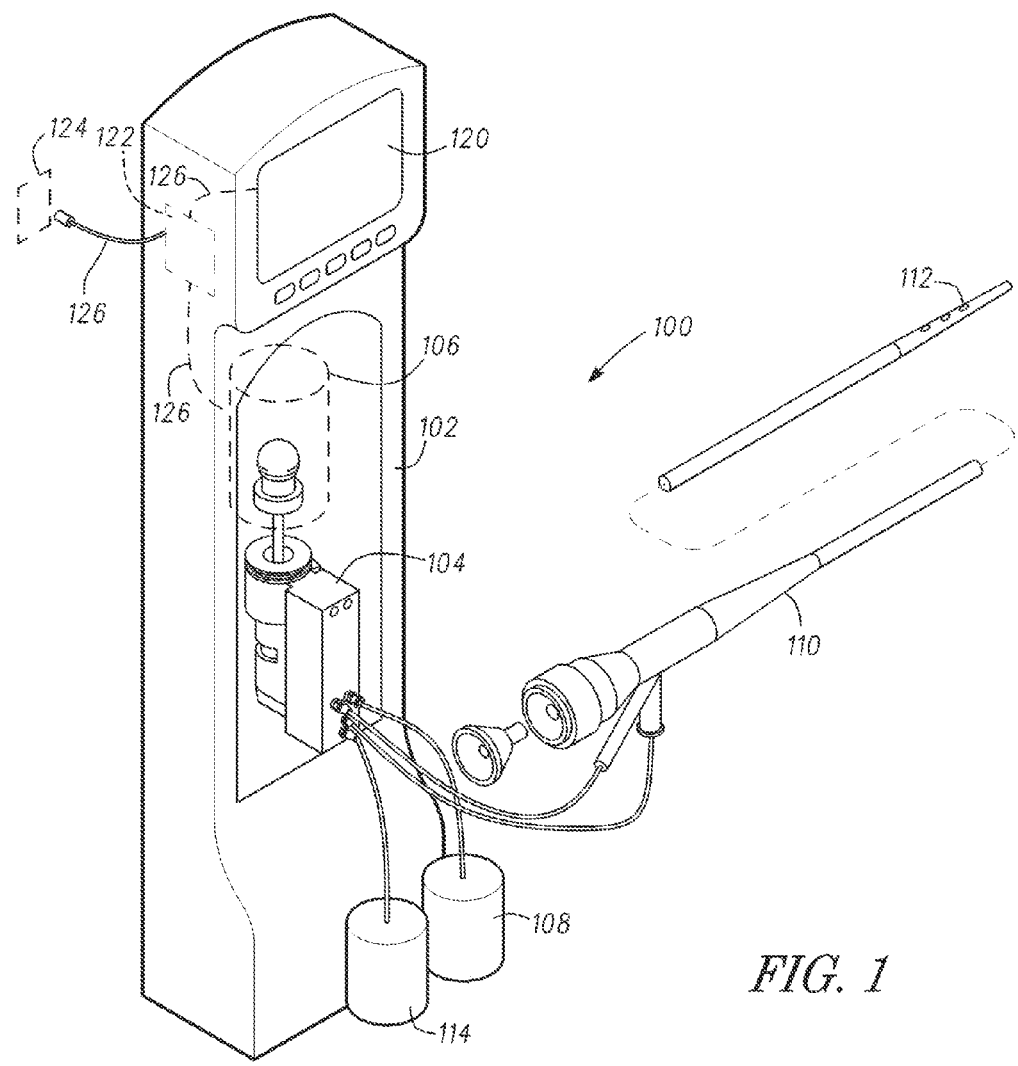
FIG. 1 is a schematic view of one example of an infusion system.

FIG. 1 is a schematic view of one example of an infusion system 100. The infusion system 100 includes a pump operator 102 coupled with a double action infusion pump 104. In the example shown in FIG. 1 the double action infusion pump is a reciprocating pump having a piston moving within a cylinder. The infusion system 100, for instance the pump operator 102, includes a drive mechanism 106 with at least a pump motor configured to couple with the piston of the double action infusion pump and accordingly reciprocate the piston within the cylinder of the double action infusion pump. The pump operator 102 includes a user interface 120, a controller 122 (e.g., a hardwired or software based processor), optionally an external interface 124, and communication paths 126 providing interfaces therebetween and with the drive mechanism 106. In one example, communication paths 126 are provided with wired connections between these components. In another example, the communication paths 126 are supplied by an interface, such as a bus, providing an array of connections between each of the components.

As will be described herein the double action infusion pump 104 provides a continuous flow of fluid, for instance infusion fluid, to a catheter such as the catheter 110 shown in FIG. 1. The computer and controller 122 enable the execution of one or more of control or compensation algorithms discussed herein. The double action infusion pump 104 provides a continuous flow of fluid instance with reciprocation of the piston of the pump 104 by evacuating first and second pump chambers within the cylinder separated by the movable piston. The structure and operation of the double action infusion pump 104 will be described in further detail herein.

The output of the double action infusion pump 104 is in one example a substantially continuous output of fluid (e.g., saline, lytics or the like) provided to the catheter 110. In one example, the catheter 110 includes one or more infusion ports 112 shown in FIG. 1. The continuous output of fluid (e.g., with some fluctuation at the top and bottom of the piston travel) from the double action infusion pump 104 is correspondingly delivered to the infusion ports 112. Accordingly, a continuous flow of infusion fluid through the infusion ports 112 is provided (e.g., with some fluctuation from a steady state flow rate).

Referring again to FIG. 1, in another example a fluid source 108 is coupled with the catheter 110. For instance the fluid source 108 is coupled with the double action infusion pump 104 and is delivered through the double action infusion pump 104 to infusion ports 112. The infusion system 100 includes an effluent reservoir 114 configured to receive an effluent provided by the catheter 110 (including in one example an entrained particulate therein). In another example, for instance where the catheter 110 is a contrast injecting catheter, the infusion system 100 does not include the effluent reservoir or it is optional. Optionally, the double action infusion pump 104 is a unitary pump module having a unitary pump body including for instance one or more aspiration inlets and outlets configured to direct a flow of aspirated fluid (effluent) from the catheter 110 through a module including the double action infusion pump as well as the aspiration inlet and outlet fittings. As shown in FIG. 1, the effluent reservoir 114 is coupled with the double action infusion pump 104 and is accordingly in communication with the catheter 110, for instance an aspiration lumen extending through the catheter 110.

Figure 2:
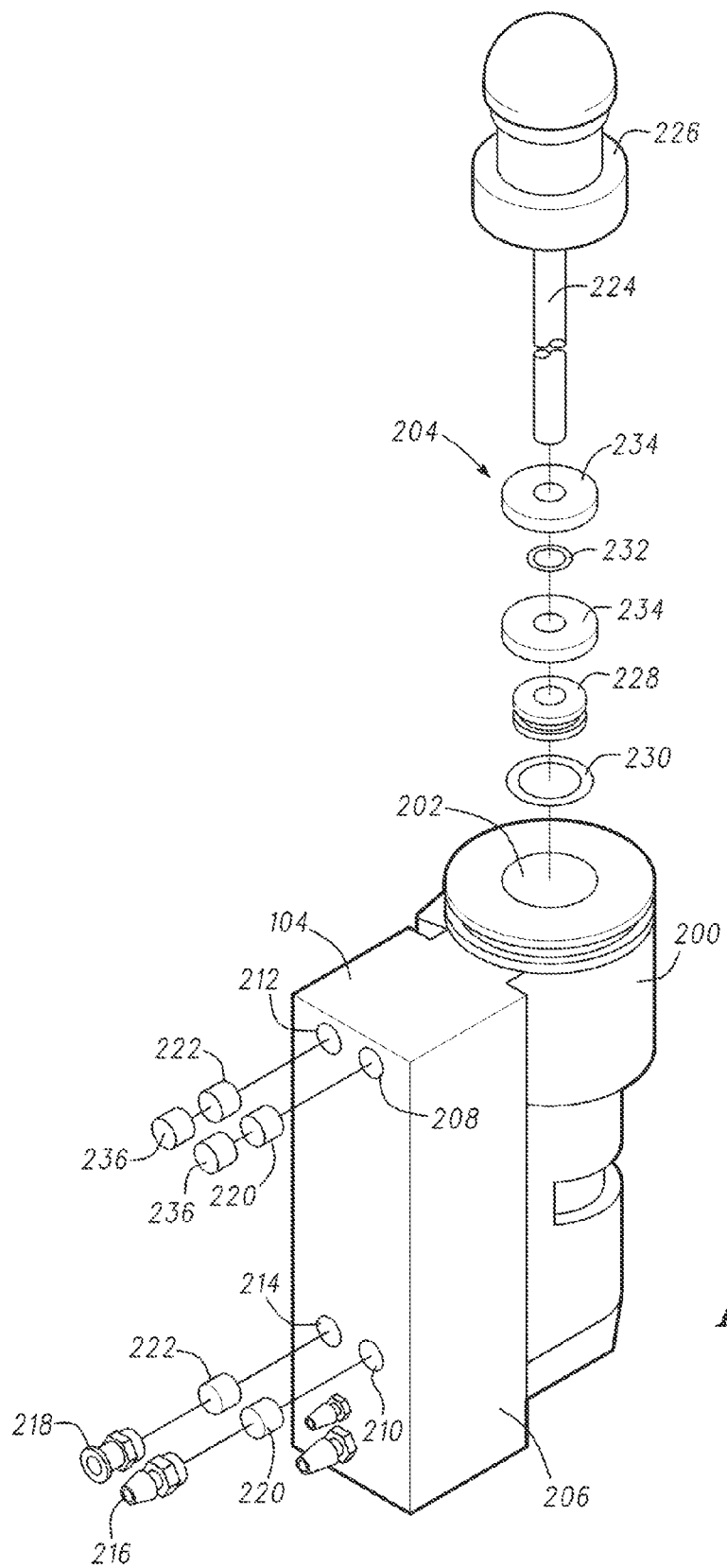
FIG. 2 is an exploded view of one example of a double action infusion pump.

FIG. 2 shows an exploded view of the double action infusion pump 104. As shown, the double action infusion pump 104 includes a pump body 200, for instance a unitary pump body formed from a single continuous piece of material. In the example, the cylinder 202 and the pump manifold 206 are formed as a single piece of material, for instance from a molded polymer resin. Where the double action infusion pump 104 is constructed with a polymer, in one example the cylinder 202 diameter and the corresponding piston 204 diameter are enlarged to provide a high flow rate at low pressures. Accordingly polymer fittings at the inlets and outlets, and the structural integrity of the cylinder 202 and the piston 204 are maintained while relatively high flow rates are realized. Optionally, the pump body 200 is machined from aluminum, steel or the like. Accordingly, the cylinder 202 and the corresponding inlets and outlets have increased structural integrity and the corresponding pump 104 is operable at higher pressures and corresponding flow rates, or at higher pressures with a smaller cylinder 202 and piston 204.

As further shown in FIG. 2, the double action infusion pump 104 includes a piston 204. In one example the piston 204 is a multicomponent piston including a series of seals configured to provide a sealing engagement between a piston disc 228 and the cylinder 202. The double action infusion pump 104 includes a series of inlets and outlets in communication with first and second pump chambers formed by the movable piston 204 and the cylinder 202. The contemporaneous evacuation and filling of each of these pump chambers accordingly provides a continuous output of infusion fluid for instance through a manifold outlet fitting 218 described in detail herein.

Referring again to FIG. 2, the piston 204 is shown in an exploded configuration. In the example shown the piston 204 includes a piston shaft 224 having a piston fitting 226. The piston fitting 226 is sized and shaped for engagement with a pump motor, such as the pump motor 106 shown in FIG. 1. The piston shaft 224 extends to a piston seat 234 sized and shaped to engage with a shaft seal 232 sized and shaped to maintain a fluid seal between the piston shaft 224 and at least the first pump chamber provided between the piston 204 and the piston seat 234. For instance, in one example a shaft seal 232 is sandwiched between dual portions of the piston seat 234 to accordingly provide a tight seal against the piston shaft 224 and accordingly prevent the egress of fluids from the cylinder 202. The piston shaft 224 is slidably received within the piston seat 234 and the shaft seal 232 and is coupled at an opposed end to the piston disc 228. In the example shown, the piston disc 228 includes a piston seal 230 sized and shaped to engage in sliding movement along the cylinder 202. In one example, the piston seal 230 is an o-ring received within grooves of the piston disc 228. In another example, the piston seal 230 is integrally formed with the piston disc 228. The piston 204, including for instance the piston disc 228 and the piston seal 230, bifurcates the cylinder 202 into first and second pump chambers.

Referring again to FIG. 2 the cylinder 202 is in communication with a first fluid inlet 208 and a first fluid outlet 212 extending through the pump manifold 206. Similarly the second pump chamber (positioned relatively below the piston 204) is in communication with a second fluid outlet 214 and a second fluid inlet 210. The pump manifold 206 in another example includes a manifold inlet fitting 216 and a manifold outlet fitting 218. The manifold inlet fitting 216 is optionally in communication with the first fluid inlet 208 and the second fluid inlet 210. As will be shown for instance in FIG. 3, the manifold inlet fitting 216 is coupled with each of these fluid inlets 208, 210 to accordingly provide a source of fluid for each of the first and second pump chambers. In a similar manner, the manifold outlet fitting 218 is in communication with the first fluid outlet 212 and the second fluid outlet 214 associated with the first and second pump chambers, respectively. The manifold outlet fitting 218 is accordingly configured to couple with the catheter 110 shown in FIG. 1 and provide the continuous output of fluid flow from the pump 104 to the one or more infusion ports 112.

As further shown in FIG. 2 the double action infusion pump 104 includes a plurality of unidirectional valves provided in each of the inlets and outlets to accordingly ensure a unidirectional flow of fluid form each of the pump chambers. For instance, the first fluid inlet 208 includes a unidirectional inlet valve 220. In a similar manner, the second fluid inlet 210 includes a unidirectional inlet valve 220. The unidirectional inlet valves 220 (e.g., check valves) allow the inflow of fluid for instance into the cylinder 202 including the respective first and second pump chambers.

In a similar manner, the first and second fluid outlets 212, 214 correspondingly include unidirectional outlet valves 222. The unidirectional outlet valves 222 cooperate to ensure evacuating fluid from the cylinders 202 is delivered out of the first fluid outlet and the second fluid outlet 212, 214 and is not otherwise backflowed into the cylinder 202, for instance during reciprocation of the piston 204 while filling of either of the first and second piston chambers. Stated another way, the unidirectional inlet valves 220 and the unidirectional outlet valves 222 cooperate to provide a one way flow of fluid from each of the first and second pump chambers provided within the cylinder 202 and separated by the piston 204. Accordingly, through reciprocation of the piston 204 a flow of fluid is continuously provided from either of the first and second fluid outlets 212, 214 throughout reciprocation of the piston 204.

Optionally, the unidirectional inlet and outlet valves 220, 222 are reversed. In the reversed configuration the double action infusion pump 104 is operable as a vacuum pump. For instance, in one example, the double action infusion pump 104 or a second instance of the pump is used as an aspiration pump to accordingly draw fluid (e.g., saline and body fluids with entrained particulate) to the effluent reservoir 114. Optionally, the pump in the vacuum configuration is coupled with the effluent reservoir 114 and applies a negative pressure within the reservoir to accordingly apply suction (e.g., to an aspiration lumen or catheter lumen of the catheter 110).

Figure 3:
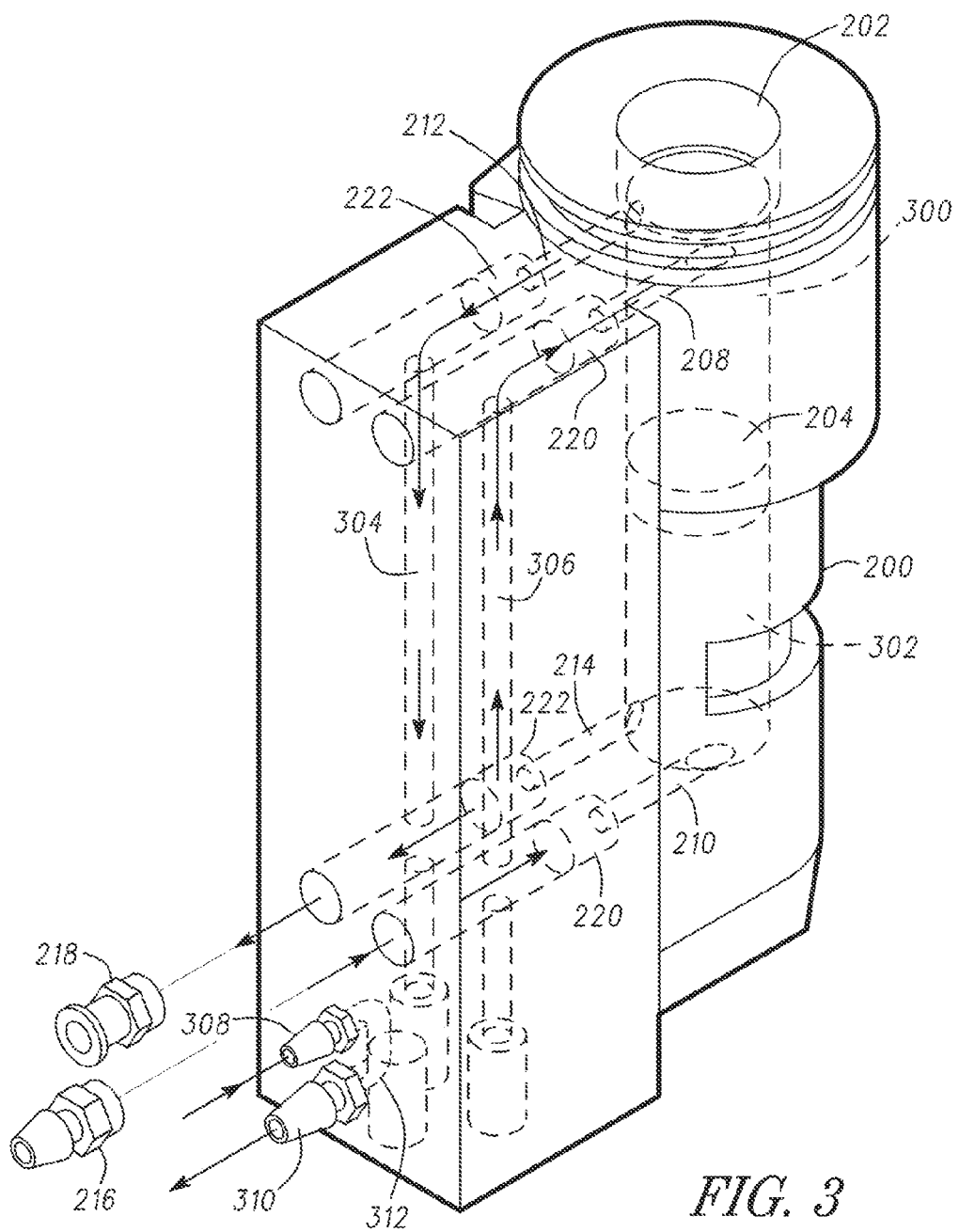
FIG. 3 is a cross sectional view of the double action infusion pump of FIG. 2.

FIG. 3 shows another perspective view of the double action infusion pump 104 previously shown in FIG. 2. In this view the interior of the infusion pump is provided in broken lines. For instance the cylinder 202 is shown divided by the piston 204 received therein. As shown in FIG. 3, the cylinder 202 is accordingly divided into a first pump chamber 300 and a second pump chamber 302. The first pump chamber 300 is in communication with the first and second fluid inlet and outlet 208, 212. In a similar manner, the second pump chamber 302 is in communication with the second fluid inlet and second fluid outlet 210, 214. As previously described each of the first fluid inlet and second fluid inlet 208, 210 are in one example in communication with a manifold inlet fitting 216. For instance, an inlet interconnect 306 formed within the pump manifold 206 provides communication between each of the first fluid inlet 208 and the second fluid inlet 210. In one example the manifold inlet fitting 216 is in communication with the fluid source 108 previously shown in FIG. 1.

In a similar manner to the first and second fluid inlets 208, 210, the first and second fluid outlets 212, 214 are in communication optionally with one another by way of an outlet interconnect 304. As shown in FIG. 3 each of the outlets 212, 214 are in communication by way of the interconnect 304 and accordingly provide their outputs through the manifold outlet fitting 218, for instance to the catheter 110 as shown in FIG. 1. In another example, each of the first and second fluid inlets 208, 210 and the first and second fluid outlets 212, 214 are respectively interconnected directly with a catheter such as the catheter 110. For instance the pump manifold 206 houses each of the inlets and outlets and accordingly allows for separate communication of each of the inlets and outlets with the corresponding catheter 110 or fluid source 108.

As further shown in FIG. 3 and as previously described herein, in one example the pump body 200 is a unitary pump body combining one or more features into a modular component assembly configured for installation within the pump operator 102 including the pump motor 106 shown in FIG. 1. That is to say, the double action infusion pump 104 including for instance a unitary pump body 200 is loaded as a single module into pump operator 102 and coupled with the catheter 110 as well as an effluent reservoir 114.

In one example, the pump operator 102 includes an aspiration pump such as a roller pump, a diaphragm pump or the like interposed between the effluent reservoir 114 and the double action infusion pump 104. The effluent pump provides a source of aspiration (e.g., a vacuum) within the catheter 110 and accordingly moves an effluent fluid (e.g., a returning fluid from the catheter 110 including for instance thrombus or plaque particulate therein) through the unitary pump body 200 and thereafter into the effluent reservoir 114. As shown in FIG. 3 in one example the pump body 200 in one example includes an aspiration inlet 308 and an aspiration outlet 310 formed in the pump body 200. As further shown in the figure an aspiration passage 312 provides communication between each of the aspiration inlet and the aspiration outlet 310. Accordingly, the aspiration inlet and outlet 308, 310 cooperate to provide an effluent passage through the pump body 200. The modular pump body 200 installed within the pump operator 102 accordingly facilitates communication from the fluid source 108 to the catheter 110 and from the catheter 110 to the effluent reservoir 114.

Figure 4A:
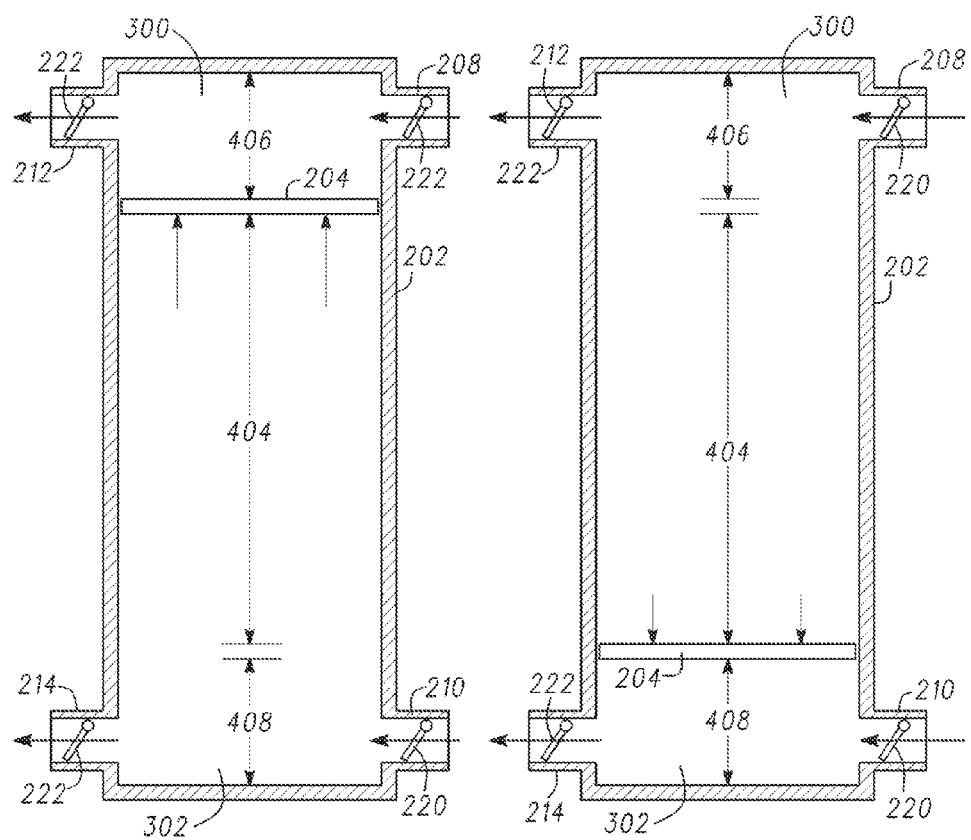
FIG. 4A is a schematic diagram showing a cylinder and piston of the double action infusion pump in two configurations.

Referring now to FIG. 4A the cylinder 202 previously shown in FIGS. 2 and 3 is shown in dual schematic representations with the piston 204 in an upward position in the leftmost view and the piston 204 in a lower position in the rightmost view. In both views the cylinder 202 includes first and second pump chambers 300, 302 formed by the piston 204 and the cylinder 202. As shown between the two views the first and second pump chambers 300, 302 have variable volumes according to the movements of the piston 204. The cylinder 202 includes first and second fluid inlets 208, 210 and first and second fluid outlets 212, 214. Each of the pairs of fluid inlets and outlets are associated with one of the first and second pump chambers 300, 302 as shown in each of the schematic views. As further shown in the schematic views each of the inlets and outlets include corresponding unidirectional inlet valves 220 and unidirectional outlet valves 222 such as check valves. Check valves facilitate in the example of the unidirectional inlet valve 220 filling of each of the respective first and second pump chambers 300, 302. In contrast the unidirectional outlet valves 222 associated with the first and second fluid outlets 212, 214 facilitate the evacuation of each of the first and second pump chambers 300, 302 for instance as the fluid within each of the chambers is pressurized during reciprocation of the piston 204.

In operation the piston 204 is reciprocated within the cylinder 202 to accordingly fill and evacuate each of the first and second pump chambers 300, 302. For instance, in the leftmost view the piston 204 is shown in an ascending configuration. In this configuration fluid within the first pump chamber 300 is pressurized and delivered through the first fluid outlet 212. In a converse manner, as the piston 204 ascends the second pump chamber 302 is filled for instance by a flow of fluid through the unidirectional inlet valve 220 of the second fluid inlet 210. Accordingly, as one of the first or second pump chambers 300, 302 is filling the opposed chamber is evacuating. The rightmost view of FIG. 4A shows the piston 204 in a descending configuration. In this configuration the first pump chamber 300 is filling for instance through the first fluid inlet 208 while the second pump chamber 302 is evacuating for instance by pushing pressurized fluid through the second fluid outlet 214.

According to the views shown in FIG. 4A a near continuous flow of fluid from the double action infusion pump 104 is provided, for instance as one of the first or second pump chambers 300, 302 is filling and the other is evacuating. Because one of the first and second pump chambers is evacuating during ascent or descent of the piston 204 a substantially continuous output is provided from the double action infusion pump (excepting a momentary pause at the top and bottom of the piston 204 travel). Similarly while one of the chambers is evacuating the other of the two chambers 300, 302 is filling to accordingly facilitate the continued delivery of fluid upon reciprocation of the piston 204 in the opposed direction.

Referring again to FIG. 4A the piston 204 is shown moving through various segments of the cylinder 202. In one example, an intermediate segment 404 spans a portion of the length of the cylinder 202 between top and bottom zones 406, 408. The intermediate segment 404 assumes the majority of the length of the cylinder 202 in an example. In another example, the intermediate segment 404 forms some portion of the cylinder 202 less than or equal to half of the cylinder length. As shown in FIG. 4A, the intermediate segment 404 spans between positions near the inlets and outlets 208, 210, 212, 214 but is spaced from the inlets and outlets relative to the top and bottom zones 406, 408 that are more closely positioned relative to the respective inlets and outlets.

As previously described the piston 204 is reciprocated. Stated another way the piston 204 is moved in a first direction such as an ascending direction (the left view of FIG. 4A) to deliver pressurized fluid from the first pump chamber 300 for instance to a catheter such as the catheter 110 as shown in FIG. 1. Once the piston 204 is moved into an upward configuration for instance toward the end of the top zone 406 the piston 204 is reversed and moved in a second direction such as the descending configuration shown in the right view of FIG. 4A and eventually travels through the bottom zone 408. Accordingly, fluid within the second pump chamber 302 is pressurized and delivered through the second fluid outlet 214.

As the piston 204 reaches the top and bottom of its travel the piston experiences a momentary pause before it begins its reversed movement in the opposed direction. In one example, the double action infusion pump 104 described herein is configured to accelerate the movement of the piston 204 within each of the top and bottom zones 406, 408 relative to the intermediate segment 404 to attenuate the pause in the piston 204 and the according pause in delivery of fluid for instance from the first and second fluid outlets 212, 214. Stated another way, by accelerating the piston 204 in the top and bottom zones 406, 408 to a second speed greater relative to a first speed within the intermediate segment 404 the output from the first and second fluid outlets 212, 214 (e.g., a flow rate) is increased within the top and bottom zones 406, 408. Accordingly, a greater volume of fluid output from the double action infusion pump 104 is provided within the zones 406, 408 that allows for the maintenance of a substantially continuous output from the double action infusion pump 104 with only moderate variation in the overall output. The fluid flow delivered by catheter 110 for instance a contrast injecting catheter, thrombectomy catheter and the like is corresponding substantially continuous (e.g., having minor fluctuations) lagging behind the corresponding fluctuations in the substantially continuous output of the double action infusion pump 104.

In one example, the piston 204 within the intermediate segment 404 moves at a first piston speed, for instance a piston speed of around 0.01 inches to around 2 inches per second. At an interface between the top and bottom zones 406, 408 with the intermediate segment 404 the piston 204 accelerates or changes its speed to a second higher speed. The output of the double action infusion pump 104 correspondingly increases with the increased speed of the piston 204.

Optionally, as the piston 204 continues to ascend or descend within the respective top and bottom zones 406, 408 the speed within these zones is further increased for instance from an initial piston speed at the interface to a terminating piston speed near the end of each of the zones 406, 408. Accordingly, the fluid flow rate of the double action infusion pump at least within the top and bottom zones 406, 408 continues to rise as the piston 204 approaches the ends of the respective zones. In a similar manner, upon reaching the end of each of the zones the piston 204 reverses direction and begins moving again through the top or bottom zones 406, 408 toward the intermediate segment 404. Optionally the piston 204, while departing from the end of each of the top and bottom zones 406, 408, accelerates within the top and bottom zones 406, 408 to accordingly increase its output and maintain a near steady state constant volume of flow for the double action infusion pump 104. In still another example, the speed of the piston 204 on an upstroke (e.g., the leftmost view of FIG. 4A) is higher in one or more of the intermediate segment 204 or the top and bottom zones 406, 408 relative to the corresponding speeds of the downstroke to account for the change in volume caused by the piston shaft 224 (as shown in FIG. 2). Accordingly, by varying speed between the upstroke and downstroke a substantially continuous output of fluid from the pump 104 and flow of fluid at the catheter 110 are achieved.

Figure 4B:
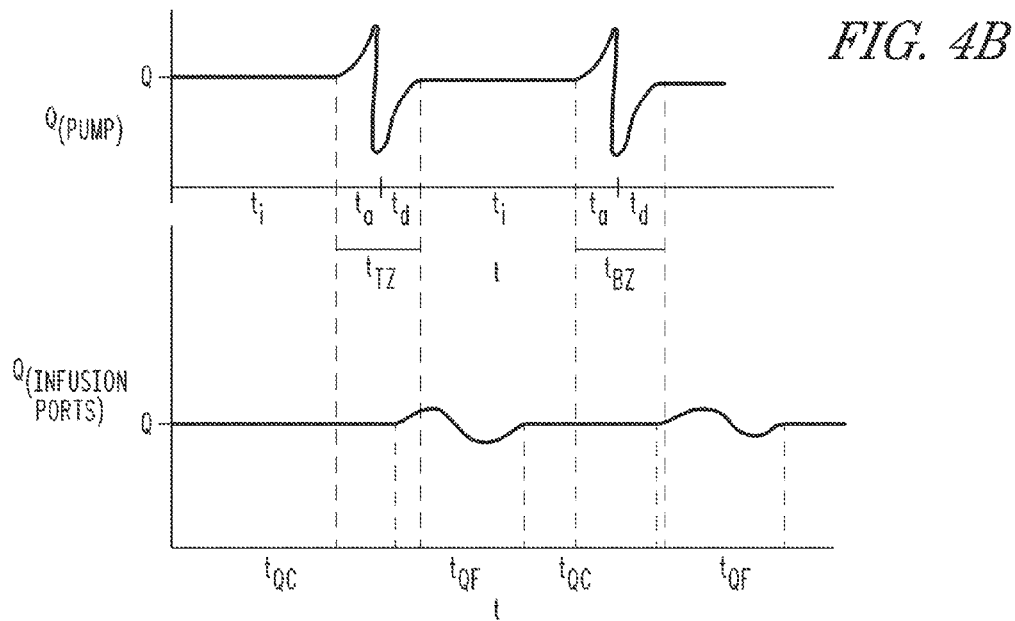
FIG. 4B is a diagram showing the respective continuous flow rates of the double action infusion pump and a catheter in communication with the double action infusion pump.

Referring to FIG. 4B, the output of the pump 104 for instance a value Q corresponding to the flow rate of the double action infusion pump 104 is plotted relative to a flow rate (Q of the infusion ports) corresponding to the output of a catheter, such as the catheter 110 shown in FIG. 1. As shown in the first plot corresponding to the flow rate of the pump 104 relative to time the flow rate of the pump is relatively constant through a time period corresponding to $t_i$ which is the time the piston 204 moves within the intermediate segment 404. As the piston moves into the top zone or bottom zone 406, 408 ($t_{TZ}$, $t_{BZ}$, respectively) and accordingly increases its speed the output of the pump accordingly rises (e.g., during a time of approach, time $t_a$). Upon reaching the end of either the top or bottom zones 406, 408 the piston pauses and then begins its descent or ascent (departs) from the top or bottom zones 406, 408, respectively. As further shown in the first plot in FIG. 4B, the flow rate immediately rises toward the intermediate segment flow rate within the segment $t_d$ (e.g., during a time of departure from the end of the top or bottoms zones 406, 408). By accelerating the piston 204 for instance raising its speed relative to a first speed within the intermediate segment 404 to a second speed in each of the top and bottom zones 406, 408 the overall output of the double action infusion pump 104 remains substantially constant, for instance rising and falling relative to a steady state output. Cessation of flow, for instance at the ends of the piston travel 204 is attenuated by way of accelerating the piston 204 within the top and bottom zones 406, 408.

The speed with which the pump 104 can make the transition from one direction to the other is affected by maximum force or torque that the pump motor 106 generates, the inertia of the motor and the rotary to linear drive (in one example a ball screw), the inertia of the piston 204 and fluid moving in the pump 104, and any mechanical gap or slop in the coupling of the drive mechanism to the pump fitting 226. The swell or capacitance of the pump 104 (e.g., natural pliability of the pump materials) will cause the pump pressure to build more slowly and result in slightly less volume being delivered per stroke when driving into a pressure restriction. The flow and the filtering (or attenuation) of changes in flow beyond the pump outlets 212, 214 is a function of piston velocity changes (see above), the capacitances of the various fluid path elements (e.g., pliability of materials, flow resistance and the like), lumped and distributed, and the fluid path attenuation, lumped and distributed. Stated another way, the path from the pump 104 to the fluid destination is an attenuating transmission line. An additional embodiment, described herein, achieves an improvement in flow transition, as seen in FIG. 9C by allowing a controlled overshoot or over velocity as well after the piston 204 direction is reversed. Accordingly, any output flow deficit (from the transition of piston movement from the first to the second direction) is made up more quickly and the downstream fluid path element capacitance is recharged more quickly, reducing the fluid deficit at the output.

Referring again to FIG. 4B the output of the one or more infusion ports 112 (the flow rate Q) is shown plotted relative to the output of the pump in the upper view. As shown the output of the infusion ports 112 lags slightly behind the output of the pump according to drag within the catheter 110 and the catheter length from the double action infusion pump 104 to the ports 112. As shown, with the substantial continuity of the pump output shown in the first view the corresponding fluid flow at the infusion ports 112 is substantially constant with only slight fluctuation around the stead state flow rate within a time period ($T_{QF}$). In the remainder of the plot of the flow rate the flow rate at the infusion ports 112 is substantially constant ($T_{QC}$).

Accordingly as shown in FIGS. 4A and 4B, by alternating filling and evacuating of each of the first and second pump chambers 300, 302 while at the same time varying the speed of the piston 204 a continuous output of fluid is provided by the double action infusion pump 104 (with slight fluctuations in the flow rate for instance corresponding to the top and bottom zones 406, 408) and a continuous flow of fluid at the one or more infusion ports 112 of the is provided (with some attenuated fluctuations corresponding to the changes in speed and the reversal of movement to the piston 204 as shown in FIG. 4A). That is to say, by changing the speed of the piston 204 the output of the double action infusion pump 104 described herein is made substantially continuous. Correspondingly, the output of the catheter 112 for instance a flow of fluid from the infusion ports 112 is also substantially continuous. Stated another way, the substantially continuous output of the double action infusion pump 104 and the catheter 110 have slight variations relative to a steady state flow rate but are otherwise continuous during the reciprocation of the piston 204 within the cylinder 202.

Figure 5:
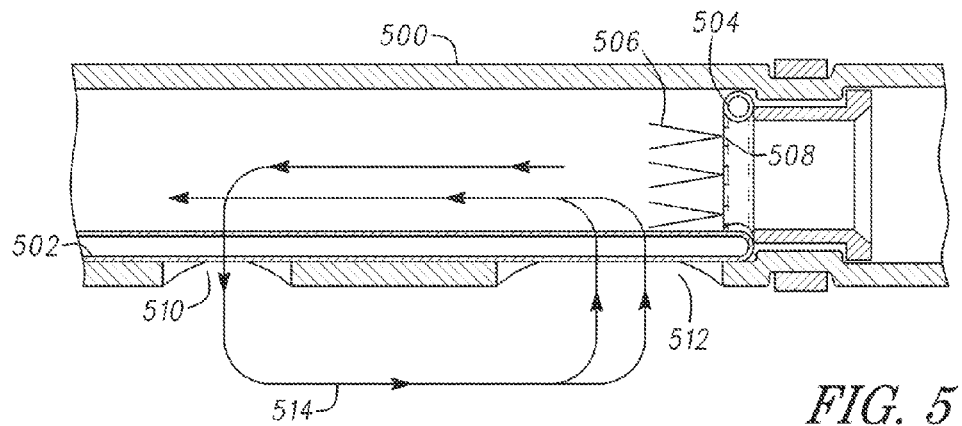
FIG. 5 is a cross sectional view of one example of a catheter distal portion of a thrombectomy catheter.

Referring now to FIG. 5 one example of a catheter, such as a distal portion 500 of the catheter 110 shown in FIG. 1 is provided. In this example the catheter 110 includes an emanator 504 positioned within the distal portion 500 of the catheter. The emanator 504 includes a plurality of infusion ports 508 arranged around a ring like structure of the emanator 504. An infusion tube such as the infusion tube 502 shown in FIG. 5 is in communication with the emanator 504 and delivers a pressurized fluid such as saline, lytics or the like to the infusion ports 508. Accordingly, one or more fluid jets 506 are formed within the catheter 110 and directed proximally for instance back toward the pump operator 102 shown in FIG. 1. The fluid jets 506 are configured to provide a proximal flow of fluid within the catheter distal portion 500. As shown in FIG. 5, the proximal flow generates a recirculating flow 514 of the fluid. For instance the distal portion of the catheter 500 includes an outflow orifice 510 and an inflow orifice 512 in communication with the flow of the fluid jets 506. The pressurized fluid jets 506 create an exterior flow of fluid through the outflow orifice 510 that allows the infused fluid to entrain particulate, such as thrombus or the like, therein and return the fluid with the entrained particulate through the outflow orifice 512 for maceration of the particulate and delivery of the particulate along the catheter 110, for instance to an effluent reservoir such as the reservoir 114 shown in FIG. 1.

In one example, the continuous output of the double action infusion pump 104 is provided by way of the infusion tube 502 to the emanator 504 to accordingly generate the fluid jets 506 and the corresponding recirculating flow 514. As previously described, the continuous output of the double action infusion pump 104 results in a corresponding continuous flow of fluid through the emanator 504 by way of the infusion tube 502. Accordingly, the recirculating flow 514 and the fluid jets 506 are substantially continuous and thereby able to generate a continuous recirculating flow 514 to ensure the reliable hydrodynamic-based removal of thrombus and particulate maceration, and further ensure continuous delivery of the entrained particulate to the effluent reservoir 114 provided in FIG. 1.

In another example, the distal portion 500 of the catheter includes direct spray infusion orifices in contrast to the recirculating flow provided with the inflow and outflow orifices 512, 510. Stated another way, the infusion tube 502 extends to the distal portion 500 and communicates with one or more infusion ports (e.g., the infusion ports 112 shown in FIG. 1). Alternatively, the infusion tube 502 communicates with an emanator like the ring type emanator shown in FIG. 5. The emanator includes peripheral infusion orifices directed through the catheter sidewall and to the exterior of the catheter. Accordingly, the emanator delivers streams or sprays of infusion fluid directly to the vasculature (e.g., thrombus within the vasculature).

Figure 6:
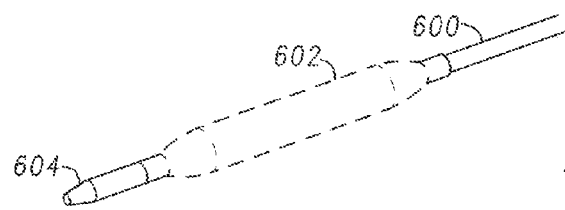
FIG. 6 is a perspective view of one example of a catheter distal portion of a contrast injecting catheter.

FIG. 6 shows another example of a distal portion 600 of a catheter, for instance in a contrast injecting catheter. As shown in the example, the distal portion 600 of the catheter includes an optional dilating balloon 602 sized and shaped to inflate within a vessel and accordingly occlude the vessel to facilitate the delivery of contrast fluid to a location of interest. The distal portion of the catheter 600 includes at least one infusion port 604, such as a contrast injecting port sized and shaped to provide a flow of contrast fluid distal to the dilating balloon 602. For instance, as previously described herein the infusion port 604 is in communication with the double action infusion pump 104. The continuous output of the double action infusion pump 104 is delivered along the catheter to the contrast infusing port 604 to accordingly deliver a contrast fluid in a continuous manner (e.g., with a continuous flow of fluid) to a location to be observed. Optionally, the infusion port is provided as a relatively large orifice, for instance within a delivery sheath or relatively large diameter catheter to accordingly facilitate delivery of the relatively viscous contrast fluid. In another example, the distal portion 600 of the catheter includes an infusion port 604 without a dilating balloon 602.

With the double action infusion pump 104 described herein, with reciprocation of a single piston such as the piston 204 shown in FIGS. 2 and 3 the pump 104 is able to generate, respectively, a substantially continuous output of fluid and substantially continuous flow of fluid from the pump and a catheter 110 coupled with the pump. Stated another way, with only minor fluctuations of an otherwise constant or static flow rate the double action infusion pump 104 is able by way of a single piston and cylinder combination 204, 202 to provide a continuous flow of fluid at one or more infusion ports 112 associated with the catheter 110 (e.g., the infusion ports 508 or the infusion port 604).

Figure 8A:
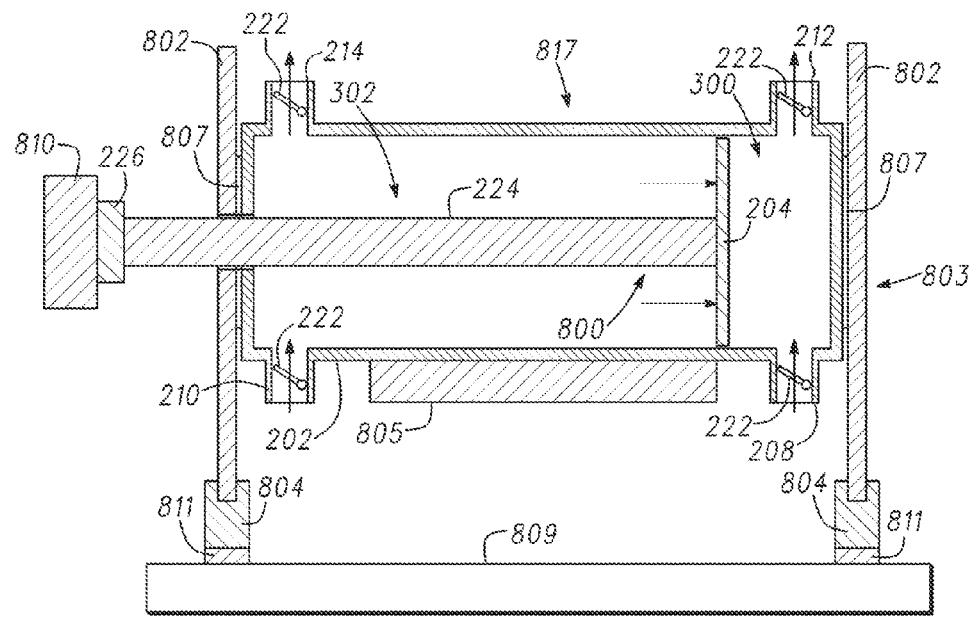
FIG. 8A is a cross sectional view of another example of a double action infusion pump.
Figure 8B:
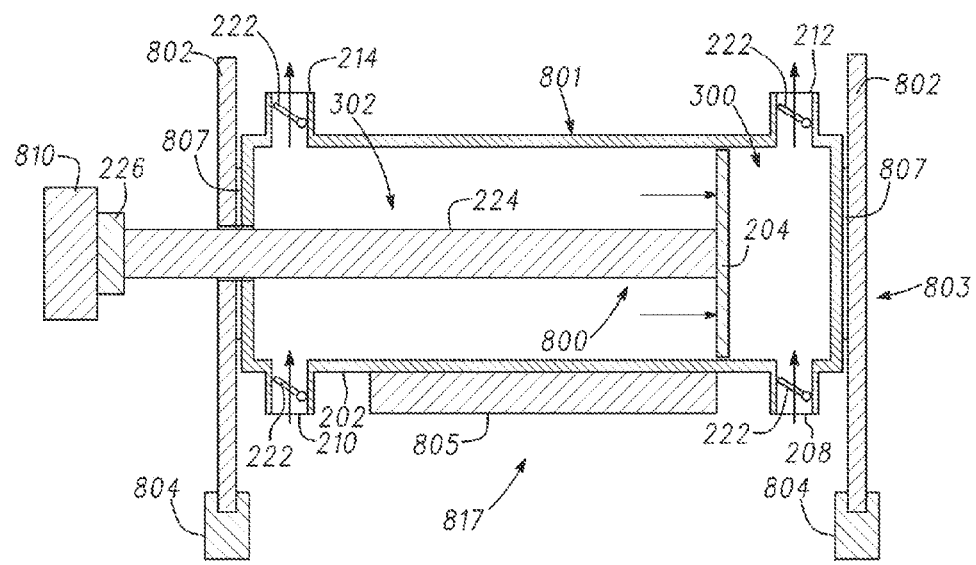
FIG. 8B is a cross sectional view of the double action infusion pump of FIG. 8A reoriented during operation.

FIGS. 8A and 8B show another example, a double action infusion pump 800 (e.g., a contrast injector pump, infusion pump or the like) of an infusion system 817. In the example, the pump 800 is provided in a horizontal configuration. In FIG. 8A, the pump 800, including the fluid outlets 212, 214 are oriented in an upward direction to facilitate purging of gas (e.g., air bubbles) from the first and second pump chambers 300, 302. FIG. 8B shows the pump 800 in an operating configuration with the fluid outlets 212, 214 oriented away from the upward direction. Any incidental gas (air bubbles) within the cylinder 202 or provided to the cylinder from the fluid inlets 208, 210 rises to an apex 801 of the cylinder and is accordingly remote relative to the fluid outlets 212, 214 and so has little or no chance of being injected into the patient.

As previously discussed above and shown in FIG. 8A, the double action infusion pump 800 is oriented so the piston 204 moves in a generally horizontal direction and the fluid outlets 212, 214 are arranged in an upward facing direction (near the top side of the pump cylinder in this orientation). The upward facing direction for the fluid outlet 212, 214 readily allows for removal of air during the priming process (e.g., priming with contrast fluid and conversely purging of air). The cylinder 202 preferably includes one or more mounting flanges 802 which engage pump mounts 804. In one example, the mounting flanges 802 and the pump mounts 804 form an outlet orientation carriage 803 configured to facilitate the orientation of the first and second fluid outlets 212, 214 (e.g., the cylinder 202 including the outlets) in the purging and operating configurations shown in FIGS. 8A, B.

The piston fitting 226 engages with the drive mechanism 810. In this example, the drive mechanism 810 includes a servo controlled motor including a ball screw and an associated controller. In one example, the drive mechanism 810 rotates in the clockwise direction to correspondingly move the piston shaft 224 and the piston 204 to the right. For movement of the piston 204 and the piston shaft 224 to the left, the drive mechanism 810 rotates in the counter clockwise direction. Optionally, at least some portion of the pump cylinder 202, the end walls of the cylinder or the like are transparent to facilitate confirmation by the operator that bubbles have been removed from the system.

The outlet orientation carriage 803 facilitates the orientation of the double action infusion pump 800 (e.g., the first and second fluid outlets 212, 214) with one or more mechanisms. In one example, the outlet orientation carriage 803 includes a cradle 805 (shown in cross section in FIGS. 8A, B) having an inner shape corresponding to an outer shape of the cylinder 202. Orientation of the cylinder 202, and accordingly the first and second fluid outlets 212, 214, relative to the cradle 805, for instance by slidable rotation, interposed bearings or the like accordingly positions the outlets 212, 214 between the purging and operating configurations.

In another example, cylinder joints 807 are interposed between the outlet orientation carriage 803 and the cylinder 202. The cylinder joints 807 provide a moving interface between the cylinder 202 and the carriage 803. The cylinder 202 is accordingly rotated relative to the outlet orientation carriage 803 with the cylinder joints 807 to position the outlets 212, 214 in the purging and operating configurations. Optionally, a locking feature, such as a detent, latch or the like is provided between the carriage 803 and the cylinder 202 to retain the cylinder 202 in the purging or operating configurations until movement to the other of the configurations is desired.

In still another example, the outlet orientation carriage 803 is movably coupled with a system base 809, for instance with one or more carriage joints 811. The carriage joints 811 rotatably couple the outlet orientation carriage (and accordingly the cylinder 202 and outlets 212, 214) to the system base 809. In the view shown in FIG. 8A, the first and second fluid outlets 212, 214 are directed upwardly to facilitate purging while the outlet orientation carriage 803 and the cylinder are held above the system base 809. In the operating configuration the outlet orientation carriage 803 and the cylinder 202 are rotated relatively below the orientation shown in FIG. 8a, for instance with the cylinder positioned below or laterally relative to the system base 809 shown in FIG. 8A to accordingly orient the first and second fluid outlets 212, 214 away from the upward direction shown in FIG. 8A. Optionally, the system base 809 is positioned above the cylinder 202 in the purging configuration, and the cylinder 202 (and carriage 803) are rotated relatively above the system base 809 to enter the operating configuration.

After the pump 800 is purged of air, the first and second fluid outlets 212, 214 are rotated (in an example) as shown in FIG. 8B so that the outlets are directed away from the upward facing direction shown in FIG. 8A. For instance, the outlet orientation carriage 803 using one of the features (joints, cradle or the like) is used to orient the cylinder 202 and the outlets 212, 214. Orientation of the outlets 212, 214 into the operating configuration and away from the apex 801 of the cylinder 202 ensures that gas (air) bubbles remaining in the cylinder 202 (or provided from the fluid source through the inlets 208, 210) are not injected into the patient. The density difference between the gas and fluid (liquid) causes bubbles to float upward (toward the apex 801) and away from the outlets 212, 214 oriented away from the upward direction. In the embodiments discussed herein, the inlet and output ports are optionally located on the same side of the pump cylinder as show in FIG. 3, or on opposing sides as shown in FIG. 4A, or at substantially any position along the cylinder 202 that allows for orientation of the outlets 212, 214 between the purging and operating configurations. In an embodiment where the inlets and outlets are near each other, the rotational orientation or position of the outlets is the important direction, being generally upward for purging of air and bubbles and generally downward for use or injection.

In an alternative embodiment, the pump shaft 224 is oriented vertically as shown in FIGS. 1 and 3. In this example, at least the pump (and optionally the drive mechanism) is rotated about a horizontal axis (e.g., with an outlet orienting carriage similar to the carriage 803 described herein) to facilitate purging of gas from the one or more of the first and second pump chambers 300, 302.

Figure 8C:
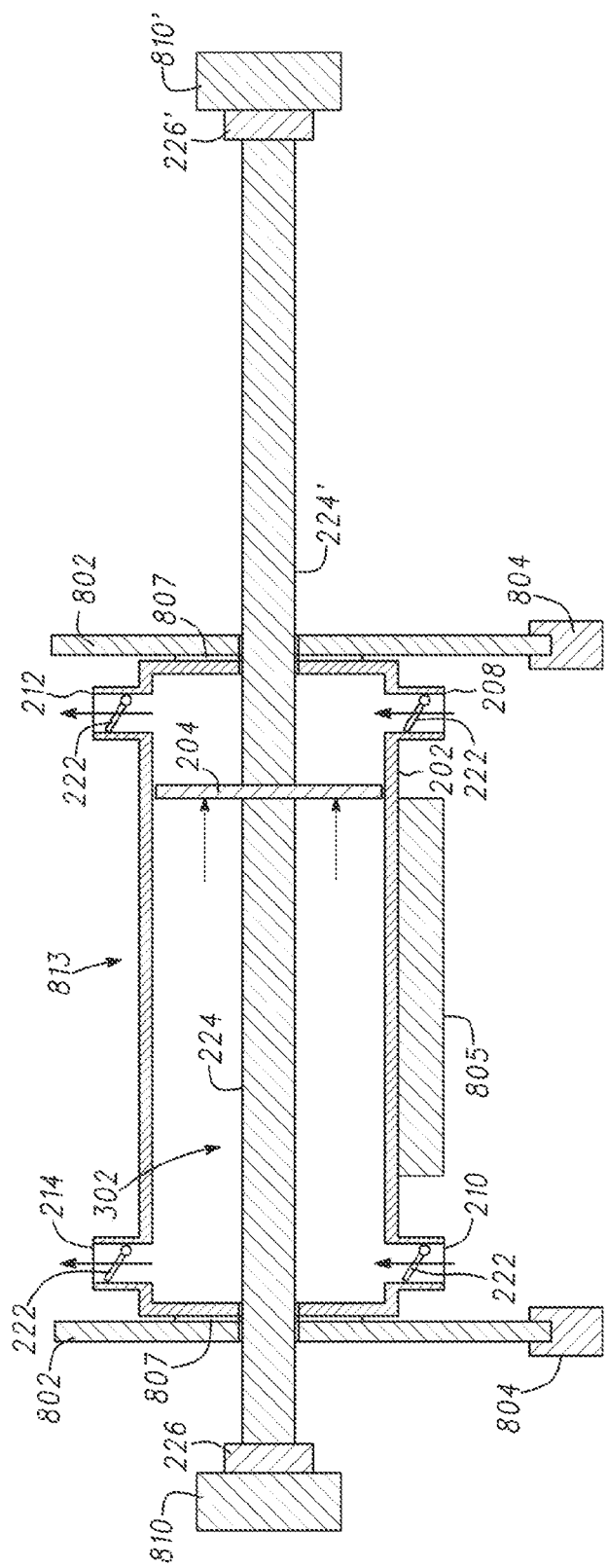
FIG. 8C is a cross sectional view of a double action infusion pump including opposed drive mechanisms.

Another example of a double action infusion pump 813 (e.g., for an infusion system 817) is shown in FIG. 8C. As shown the pump 813 includes a piston shaft extending to both sides of the piston 204 and through the ends of the cylinder 202. Optionally, the piston shaft is formed with two piston shafts 224 and 224' each coupled to the piston 204. As described herein, the arrangement shown in FIG. 8C with a shaft extending through both ends of the cylinder 202 mitigates at least one source of flow reduction. In this example, the flow reduction includes the mechanical coupling slop or gap in the gripping mechanism between a drive such as the drive mechanism 810 and the piston fitting 226. As shown in FIG. 8C, the drive mechanism 810' on the second shaft 224' includes a second motor (and associated controller). In another example, the drive mechanism 810' is a linear spring in compression that biases the piston 204 to accordingly mitigate mechanical slop in the system.

Furthermore, the shafts 224 and 224' are the preferably but not necessarily the same diameter and extend through the opposed ends of the cylinder 202 (e.g., with corresponding seals at each of the ends). By providing a piston shaft having identical diameters in each of the first and second pump chambers 300, 302 the fluid pumped per unit of distance traveled by the piston 204 is the same in both directions. Accordingly, differing control algorithms are optionally not used to ensure consistent flow on the up stroke and down stroke of the piston 204.

Figure 8D:
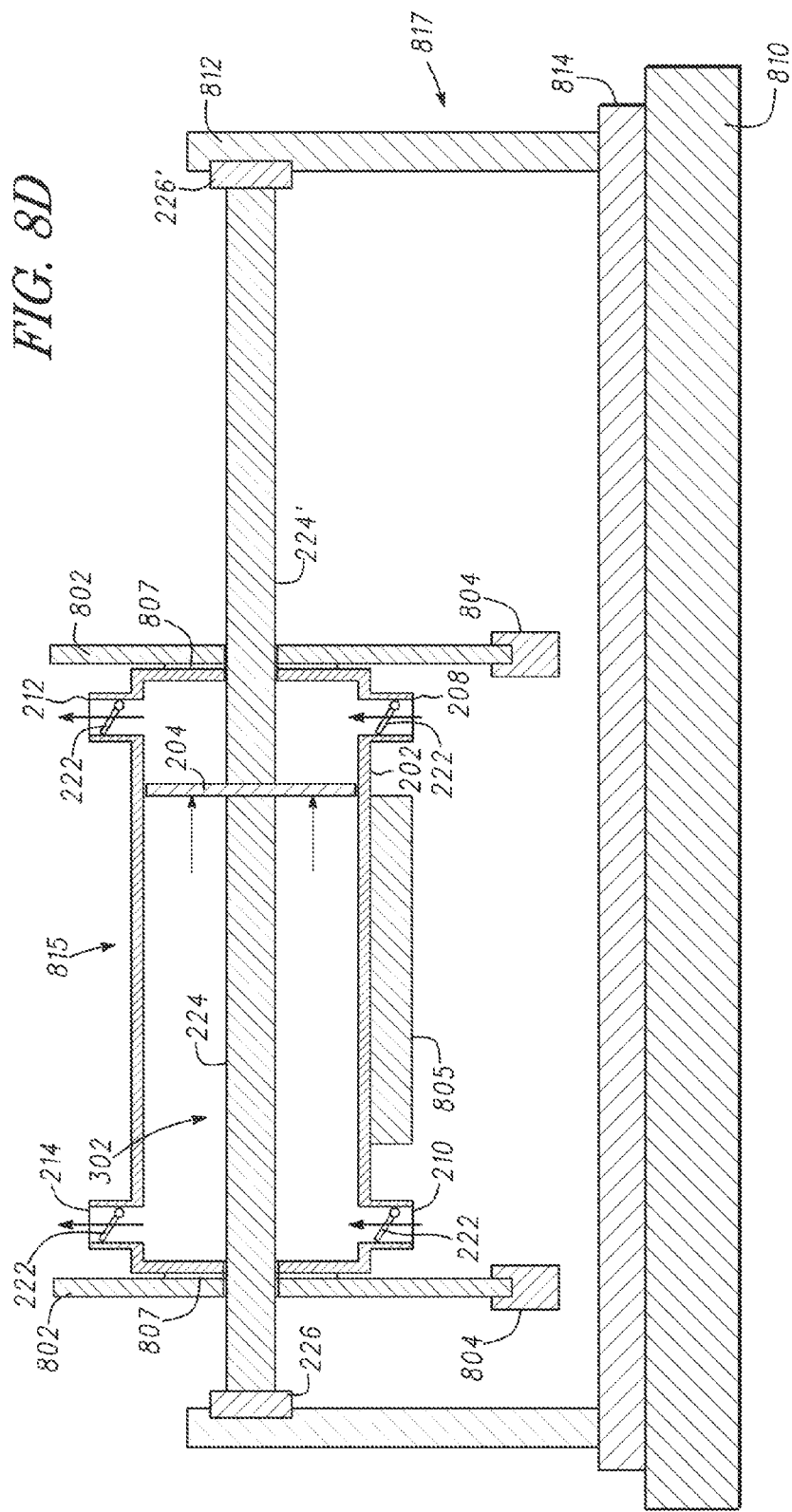
FIG. 8D is a cross sectional view of another double action infusion pump including a reversing mechanism.

Another example of a double action infusion pump 815 for an infusion system 817 is shown in FIG. 8D. At least some of the features of the double action infusion pump 815 are similar to features of the other pumps described herein. In this example, the previously described drive mechanisms 810 and 810' are replaced in part by a piston shaft carriage 812 (e.g., a C-shaped mount or clamp) coupled with each of end portions of the piston shaft 224 (and 224' with a two piece construction). Optionally, the piston shaft carriage is fastened (e.g., tightened down manually, automatically by the system, or with a biasing element) to mitigate (eliminate or reduce) the mechanical slack in the coupling to the piston shafts 224 and 224'. As shown in FIG. 8D, the drive mechanism 810 is coupled with the piston shaft carriage 812 and accordingly reciprocates the piston shaft carriage relative to the cylinder 202. In this case the piston shaft carriage 812 is coupled with a ball screw of the drive mechanism 810 and optionally with a support rail if needed. Alternatively, the interface may be in line with shaft 224.

As mentioned elsewhere, increasing the speed of the drive mechanism 810 before the transition in direction (reciprocation) and providing some velocity overshoot as the movement in the opposite direction can be used to compensate for or reduce the flow deficit during transition. A challenge to this approach and corresponding algorithms is that the higher the velocity change that is needed, the longer it takes to make that change given a maximum acceleration capability to the drive mechanism 810. As discussed herein, one approach is to limit the amplitude of the velocity increase and extent the time or duration of that increase appropriately.

In one example, the drive mechanism 810 includes a reciprocating drive mechanism (e.g., a reversible motor) configured to move the piston shaft carriage 812 and the piston shaft 224 (and optionally 224') for reciprocation of the piston 204 within the cylinder 202. In another example shown in FIG. 8D the double action infusion pump includes a reversing mechanism 814 coupled between the drive mechanism 810 and the piston shaft 224 (e.g., between the piston shaft carriage 812 and the drive mechanism 810). Optionally, the reversing mechanism 814 is formed as part of one or more of the piston shaft carriage 812 or the drive mechanism 810.

As described herein, the reversing mechanism 814 includes one or more mechanisms configured to reverse the movement of the piston shaft 224 (including the piston 204 and the piston shaft carriage 812). The reversing mechanism 814 accordingly allows for continued movement of the motor and much of the drive mechanism 810 in a single direction (e.g., rotation in a single direction) while reciprocating the piston 204. Mechanical losses and slowness of response due to inertia, mechanical slop, or the like occurring with other examples using reversing motors are thereby reduced. Instead, the reversing mechanism 814 in combination with a drive mechanism 810 operating in a single direction facilitates the continuous operation of the drive mechanism in a direction (e.g., one rotational direction) while reciprocating the piston 204 within the cylinder 202 of the double action infusion pump 815.

In one example, the reversing mechanism 814 includes a ball reverser actuator (e.g., a self-reversing screw or ball screw). One example of a ball reverser actuator is sold by Norco Inc. under the Ball Reverser trademark. The exemplary ball reverser is manufactured by MarathonNorco Aerospace, Inc. of Waco, Tex. The reversing mechanism 814 includes a cross groove shaft having at least first and second groove tracks. In one example, the cross groove shaft is coupled with the drive mechanism 810. Rotation of the drive mechanism 810 (e.g., in a single rotational direction) correspondingly rotates the cross groove shaft. A cage of the ball reverser actuator (e.g., the reversing mechanism 814) is coupled with the piston shaft carriage 812. The cage includes a plurality of balls (ball bearings therein). Rotation of the cross groove shaft carries the balls and the cage along the first or second groove track.

Near the ends of the cross groove shaft the first and second groove tracks are in communication. Continued (unidirectional) rotation of the cross groove shaft carries the balls of the cage into a turnaround transition between the first and second groove tracks. The balls are reoriented by the turnaround transition and continued rotation of the cross groove shaft accordingly moves the balls (and the cage) according to the other of the second or first groove track and thereby reciprocates the cage, the piston shaft carriage 812, the piston shaft 224 and the piston 204 in the opposed direction. Optionally, the first and second groove tracks have varying pitch to change velocity of the cage (and the piston 204 coupled with the cage). For instance, the pitch of the first and second groove tracks is increased along the portions of the tracks (e.g., ends) corresponding to the top and bottom zones 406, 408 of the cylinder 202. For intermediate segment 404 of the piston 204 movement the first and second tracks 404 have a lesser pitch to facilitate a relatively slower movement of the piston. This is advantageous for a pump with a piston rod in only one chamber, which thus requires different piston velocities in the different directions. Similarly, the pitch of the first and second groove tracks is designed to accordingly vary (accelerate or decelerate) the movement of the piston 204 to realize a desired constant output from the pump 815.

An alternative reversing mechanism 814 configured to self-reverse the reciprocating piston 204 with rotation of the drive mechanism 810 in a single direction is a rolling ring type reversal system such as that manufactured by Joachim Uhing GmbH & Co. KG of Mielkendorfand, Germany and available from Amacoil, Inc, Aston, Pa. This example of a reversing mechanism 814 includes a shaft coupled with the drive mechanism 810, such as a motor configured to provide rotation in at least one direction. A cage is coupled around the shaft and includes a plurality of rolling rings. One or more of the rolling rings has a tilted configuration. The rotating shaft biases the tilted rolling rings along the shaft and correspondingly moves the cage along the shaft. The cage is coupled with the piston shaft carriage 812 and thereby moves the piston 204 within the cylinder 202. Reversing movement of the cage is provided by moving a lever on the cage by having the lever impact a travel stop on the drive mechanism mounting. Accordingly, reciprocation of the piston 204 is realized while rotation of the drive mechanism 810 is maintained in a single rotational direction.

Optionally, the one or more rolling rings are tilted to varying degrees to accordingly change the translation speed of the cage (as well as the piston 204). By tilting the one or more rolling rings the speed of the piston 204 is thereby adjusted, for instance to adjust the output of the pump 815 toward a near continuous flow of fluid.

In operation, when the cage (including the rolling rings therein) of the reversing mechanism 814 reaches the end of its travel, the drive mechanism 810 and the shaft continue rotating at the same velocity and in the same direction while the cage (e.g., a housing, traveler or the like retaining the rolling rings) automatically reverses direction. Accordingly, the inertia of the motor and shaft are not changed. Instead, they continue to rotate in the same direction. Only the modest inertia of the shaft 224, piston 204, piston fitting 226, and the cage or optional piston shaft carriage 812 is overcome to reciprocate the piston 204.

The double action infusion pump 815 is suitable to this self-reversing mechanism (e.g., a rolling ring mechanism) because multiple passes of the piston 204 may be used to pump enough fluid for a single procedure. By using such a mechanism, the flow characteristics can be improved as illustrated in FIG. 9D. The depth of the deficit in flow is reduced because the inertial energy of the motor and some of the drive mechanism or drive train elements does not need to be reversed.

In the various embodiments discussed herein, the minimum volume remaining in the chambers 300 and 302 at the end of respective discharge strokes may vary as long as the piston does not bottom out or impact the ends of the cylinder. Thus the precise position of the pump cylinder in the mounting may vary as long as the pump cylinder does not move during pumping and the piston 204 does not bottom out on either of the end walls.

Figure 7:
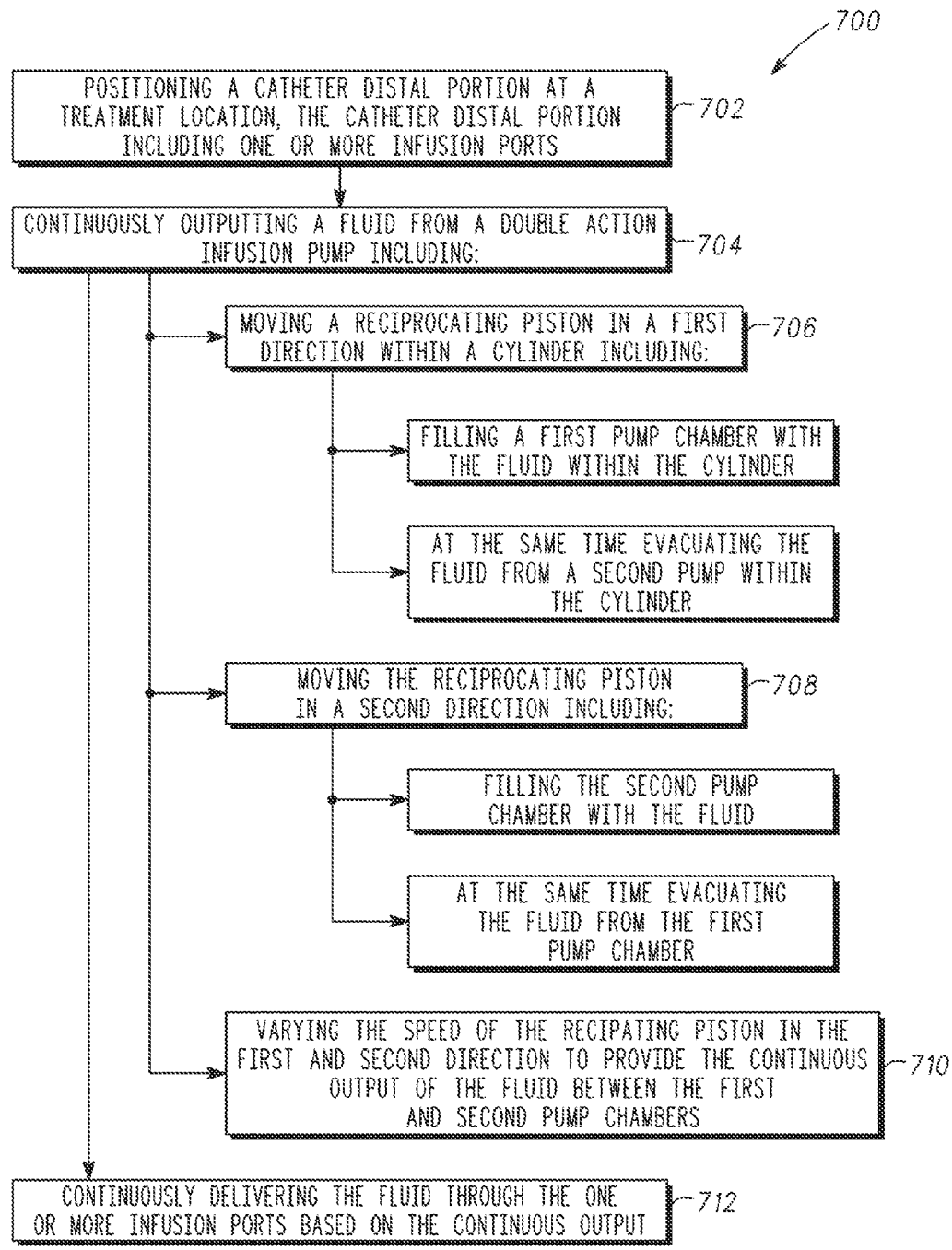
FIG. 7 is a block diagram showing one example of a method of infusing a fluid into a vessel.

FIG. 7 shows one example of a method 700 of infusing a fluid into a vessel. In describing the method 700 reference is made to one or more components, features, steps and the like described herein. Where convenient reference is made to the components, features and the like with reference numerals. The reference numerals provided are exemplary and are not exclusive, for instance the features, components and the like described in the method 700 include but are not limited to the corresponding numbered elements, other corresponding features described herein (both numbered and unnumbered) as well as their equivalents.

At 702, a catheter such as a catheter 110 shown in FIG. 1 having a catheter distal (e.g., either of the catheter distal portions 500, 600 shown in FIGS. 5 and 6) is positioned at a treatment location within the vessel. The catheter distal portion (500 or 600) includes one or more infusion ports (e.g., the infusion ports 508 and 604). As shown in FIGS. 5 and 6 in one example the catheter 110 shown in FIG. 1 includes a thrombectomy catheter configured to provide a recirculating flow of fluid 514 through an outflow orifice 510 and an inflow orifice 512 as shown in FIG. 5. The catheter 110 includes in another example, a contrast injecting catheter including for instance the catheter distal portion 600 shown in FIG. 6. In one example the contrast injecting catheter includes a dilating balloon 602 as well as an infusion port 604 sized and shaped to deliver a contrast fluid distally relative to the dilated balloon 602.

At 704, the method includes continuously outputting a fluid from a double action infusion pump 104 in communication with a fluid source 108, such as a source of contrast fluid, infusion fluid (saline, lytics)) or the like. Continuously outputting the fluid includes moving the reciprocating piston 204 in a first direction within a cylinder such as the cylinder 202 and moving the reciprocating piston in a second opposed direction within the cylinder 202. In one example, moving the reciprocating piston includes filling a first pump chamber 300 with the fluid within the cylinder while at the same time evacuating the fluid for instance another volume of the fluid from a second pump chamber 302 also within the cylinder 202 (see the rightmost view of FIG. 4A). Accordingly, while the first pump chamber 300 is filling the second pump chamber 302 with the piston 204 moving in the first direction is accordingly evacuating to provide a first portion of flow to the catheter 110 as shown in FIG. 1.

At 708, moving the reciprocating piston in a second direction such as an opposed direction (including for instance the leftmost view of FIG. 4A) includes filling the second pump chamber 302 with the fluid for instance the fluid provided by the fluid source 108 shown in FIG. 1. At the same time the first pump chamber 300 is evacuated, for instance by the piston 204 collapsing the first pump chamber 300 and accordingly delivering fluid from one of the two fluid outlets 212, 222 as shown in FIG. 4A. Accordingly, and in a similar manner to reciprocation of the piston in the first direction, reciprocation of the piston 204 in the second direction correspondingly fills the second pump chamber as the first pump chamber is evacuated. With reciprocation of the piston in the first and second directions a substantially continuous output of fluid is provided.

At 710 the method 700 further includes varying the speed of the reciprocating piston 204 in the first and second directions to provide the continuous output of the fluid between the first and second pump chambers 300, 302. That is to say, in one example the piston 404 is moved along an intermediate segment 404 of the cylinder 202 at a first piston speed, for instance a piston speed of between about 0.01 inches to 2 inches per second. As the piston 204 enters the top and bottom zones 406, 408 the piston is accelerated and its speed is increased to a second piston speed greater than the first piston speed to accordingly increase the flow rate of the double action infusion pump 104 within the corresponding top and bottom zones 406, 408. As previously described herein, by increasing the flow rate of the double action fusion pump 104 within each of the top and bottom zones 406, 408 (by raising the speed of the piston 204 within these zones) the output of fluid from the double action infusion pump 104 is continuous. That is to say, while there is some fluctuation near the top and bottom zones 406, 408 in the overall output of fluid, the output is substantially continuous as the piston 204 is accelerated toward the top and bottom zones 406, 408 (an optionally while departing from the top and bottom zones 406, 408) to increase the overall flow rate and thereby offset any decrease in flow rate otherwise provided by the pause of the piston 204 at the top and bottom of its movement.

At 712 fluid is continuously delivered through the one or more infusion points 112 of the catheter 110 based on the continuous output from the double action infusion pump 104. Referring to FIG. 4B, as shown with the flow rate of the pump 104 shown in the first plot adjusted according to the variations in speed of the piston 204 the corresponding output or fluid flow from the catheter infusion ports 112 is shown in the bottom plot. With the change in speed within the top and bottom zones 406, 408 the output of the double action infusion pump 104 increases in these zones to substantially realize an overall continuous output of fluid that offsets the decrease in output with the pause of reciprocation of the piston 204. Accordingly, the output of the catheter 110 for instance with the infusion ports 112 is substantially continuous and any fluctuations in the output from the double action infusion pump 104 are attenuated by drag in the catheter and connecting tubing and dispersion of the fluid within the catheter 110 to accordingly provide a substantially continuous flow rate with only minor variations (lagging those variations in the pump output).

Several options for the method 700 follow. In one example, filling of the first and second pump chambers 300, 302 with the fluid includes delivering fluid through respective first and second fluid inlets 208, 210 to the first and second pump chambers 300, 302 respectively. The first and second fluid inlets each include a unidirectional valve 220 as previously described herein. In a contrast, evacuating the fluid from the first and second pump chambers 300, 302 includes delivering fluid through the outlets 212, 214. In one example the first and second fluid outlets each include unidirectional outlet valves 222 as previously shown in FIGS. 2 and 4A.

In another example, varying the speed of the reciprocating piston 204 includes varying the speed between an intermediate segment 404 of the cylinder 202 and within top and bottom zones 406, 408 of the cylinder 202. Varying of the speed includes in one example moving the reciprocating piston 204 at a first piston speed along the intermediate segment 404 and moving the reciprocating piston 204 at a second piston speed greater than the first piston speed within the top and bottom zones 406, 408. Optionally, moving the reciprocating piston 204 at the second speed, for instance within the top and bottom zones 406, 408, includes moving the reciprocating piston 204 near an interface between the intermediate segment 404 and each of the top and bottom zones 406, 408 at an initial piston greater than the first piston speed within the intermediate segment 404. Additionally moving the reciprocating piston near ends of the top and bottom zones 406, 408 (adjacent to the end of the travel of the piston 204 in each of the reciprocating directions) includes moving at a terminating piston speed greater than the initial piston speed within the top and bottom zones 406, 408. Stated another way, the piston 204 optionally accelerates (or assumes 2 or more speeds) from between the interface between the top and bottom zones 406, 408 to the end of it travel within each of the top and bottom zones 406, 408.

In another example continuously delivering the fluid through the one or more infusion ports 112 includes continuously delivering a contrast fluid through one or more infusion ports such as the infusion port 604 shown in FIG. 6 with the contrast injecting catheter distal portion 600 shown in FIG. 6. In another example, continuously delivering the fluid through the one or more infusion ports includes generating the recirculating fluid loop such as the fluid loop 514 shown in FIG. 5. Generating the recirculating fluid loop 514 includes in one example continuously delivering the fluid through a fluid jet emanator 504 within a catheter lumen of the catheter such as the catheter distal portion 500 shown in FIG. 5. A portion of the continuously delivered fluid is provided through an outflow orifice 510 of the catheter in communication with the catheter lumen. The portion of the fluid delivered through the outflow orifice is returned through an inflow orifice 512 (with entrained particulate therein). The inflow orifice communicates with the catheter lumen and the plurality of fluid jets 506 provided by the emanator 504.

In still another example, the method 700 further includes filling a fluid source such as the fluid source 108 while continuously outputting the fluid from the double action infusion pump 104 at the same time. That is to say, the double action infusion pump 104 may be operated continuously without needing to reload the cylinder or other feature of a pump to accordingly provide a renewed flow of fluid. Instead, the fluid source 108 provides an open ended supply of fluid to the double action infusion pump 104. Accordingly, with continued refilling of the fluid source 108 as needed the double action infusion pump 104 is able to continuously output a flow of fluid from the pump 104 and accordingly provide a continuous flow of fluid from the catheter 110, for instance chronically or near chronically positioned within a patient.

FIGS. 9A-9D show approximate waveforms under various example control strategies. The upper graph in each figure shows the velocity of the motor and drive train 999 and the lower graph shows the flow 997 at the output of the pump (labeled $Q_{(pump)}$ in FIG. 4B). The nominal forward velocity 911 and reverse velocity 913 of the piston are show at corresponding horizontal dotted lines. The nominal flow at the pump is shown as a dotted horizontal line 915 in the flow diagram portion of each Figure.

The graphs of FIGS. 9A-9D include a modeling of the limitation of a maximum acceleration of the motor and drive train which causes a finite slope to exist in the transition regions, as seen in the regions 901 of the first diagrams. The modeling also includes the fact that in selected embodiments that the piston displacement per unit length is different on the side with the shaft than on the side without a shaft, in those embodiments where there is not an equivalent area shaft on both sides. This can be seen in the fact that the nominal velocity dotted line 911 in one direction differs in amplitude from the nominal velocity 913 in the other direction. For ease of illustration, the capacitance of the pump itself, the piston and fluid inertia, and the effect from delay caused by valving are not included in the model, all of which may be designed to reduced there effect using various methods know to those skilled in the art.

Referring again to FIG. 4B, as shown the downstream flow waveform is damped by the capacitance and resistance of the intervening fluid path elements. The downstream waveforms corresponding to the wave forms shown in FIGS. 9A-9D are similarly attenuated (damped) according to the capacitance and resistance of intervening fluid path elements. The downstream elements may be selected to achieve the damping needed for satisfactory performance. In other situations, the downstream elements are selected by the end user and the system has minimal (or no) control over the downstream element properties. As discussed herein, the various embodiments including control algorithms provide waveforms that are more advantageous because they cause less pulsation at the pump and thus require less dampening in the downstream fluid path.

Figure 9A:
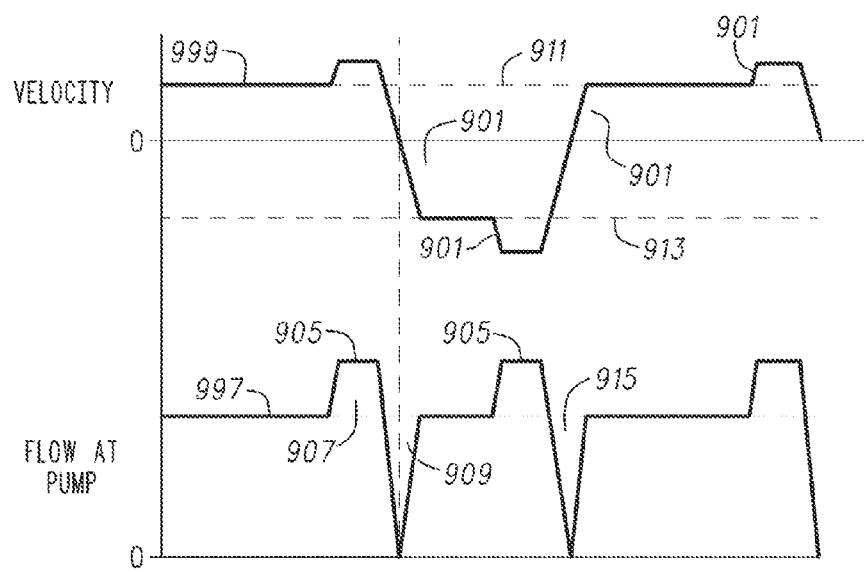
FIG. 9A is a composite velocity and flow plot using an example control algorithm for a double action infusion pump.

FIG. 9A is an example waveform based on the same control algorithm or strategy as shown in FIG. 4B, in which the compensation is achieved by an increase in volume delivery taking place before the transition. In this embodiment, there is a maximum limit to the flow increase 905 that is allowed so that the instantaneous velocity does not become unsafe for either the patient or the drive mechanism. This also limits the amplitude of the motor and drive train inertia what must be reversed. This limit may be, for example, an absolute flow or a percentage increase of the nominal flow, and there may be different limits and approaches for the patient limit as compared to that to preserve the drive mechanism. If there were no limit and the maximum acceleration is used, the velocity increase would be $1/\sqrt{2}$ or approximately 0.707 times the nominal velocity. The volume of extra flow 907 is selected to be equal to the volume of the flow deficit 909 so that the nominal flow is maintained over time. This embodiment utilizes a single sided or ended shaft, shown for instance in FIG. 8A. Accordingly, the output volume per unit length is lower in the reverse direction than the forward direction. Thus to have equal flow rates, the nominal velocity in the reverse direction 913 is greater than the nominal velocity in the forward direction 911

Figure 9B:
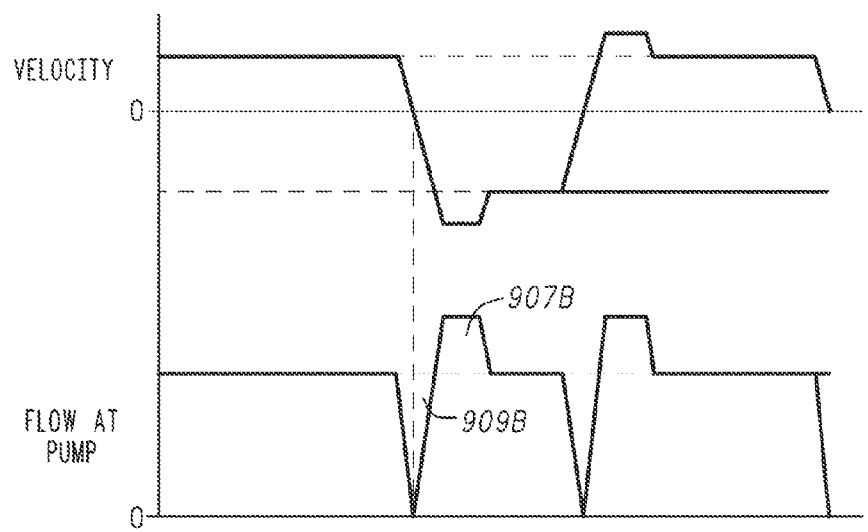
FIG. 9B is a composite velocity and flow plot using another example control algorithm for a double action infusion pump.
Figure 9C:
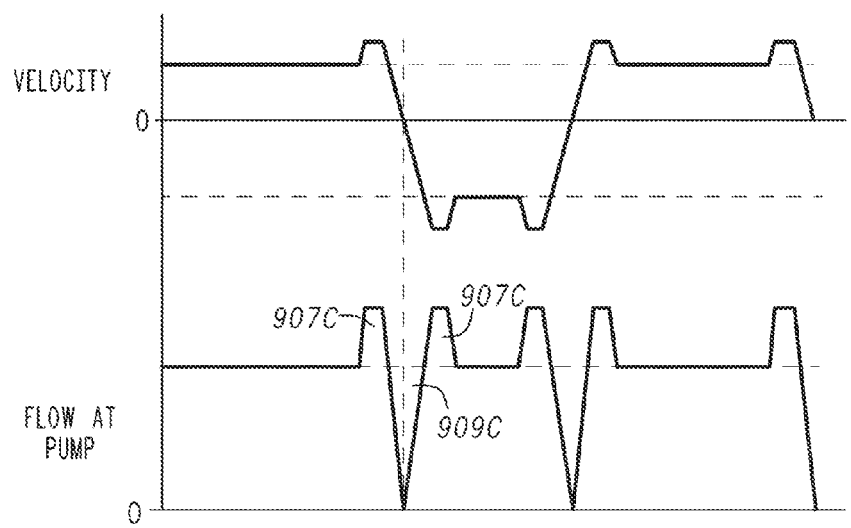
FIG. 9C is a composite velocity and flow plot using yet another example control algorithm for a double action infusion pump.
Figure 9D:
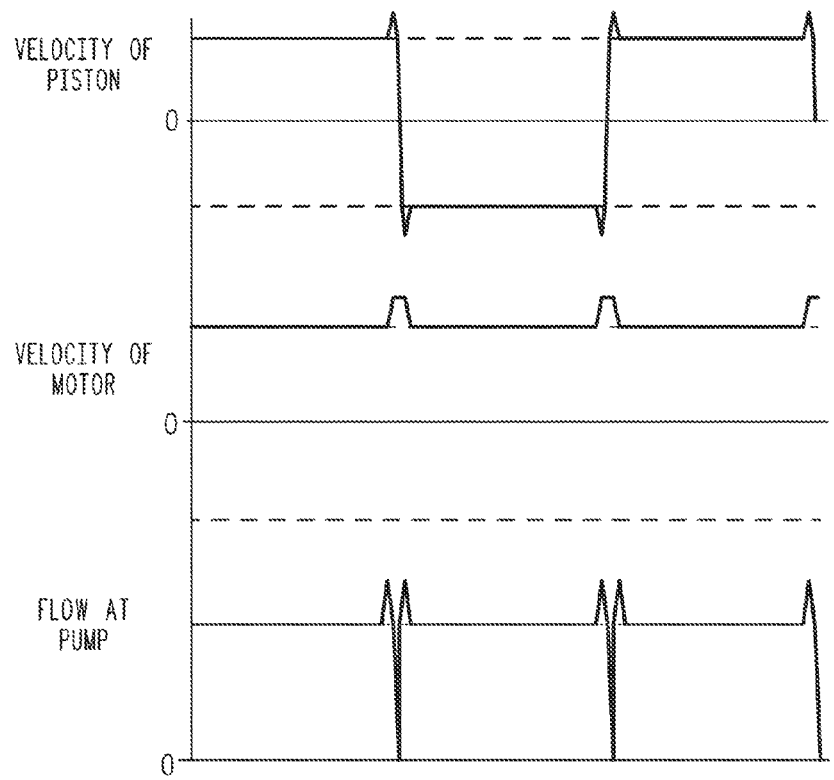
FIG. 9D is a composite velocity and flow plot using still another example control algorithm for a double action infusion pump.

FIG. 9B is an example waveform corresponding to a control algorithm that increases the flow rate immediately after the transition to realize flow compensation. The volume of extra flow 907B is selected to be equal to the volume of the flow deficit 909B so the nominal flow is delivered. This algorithm accordingly utilizes the overshoot that occurs when operating a servo system at high or maximum acceleration to offset a flow reduction otherwise caused with reciprocation.

FIG. 9C is an example waveform corresponding to a control algorithm that increases the flow rate both immediately before and immediately after the transition. The volumes of extra flows 907C are selected so that when combined, their total volume equals the volume of the flow deficit 909C to ensure nominal flow is delivered. This waveform is more quickly damped by the attenuation of the fluid delivery line than the single sided compensation of FIG. 9A or 9B.

FIG. 9D is an example waveform corresponding to a control algorithm used in combination with a motor independent reversing mechanism 814 that maintains a single direction of motor movement while reversing the piston motion. Thus the only inertia to overcome is that of the piston, shaft, carriage, reversing mechanism and fluid in the pump (without the need to overcome the significant inertia of the motor and drive shaft). Because this is significantly less inertia than that of the drive train elements, e.g the motor and drive shaft, the maximum acceleration available to be applied to the reversing components is much greater than in the embodiments of FIGS. 9A, 9B, and 9C. In the embodiment shown in FIG. 9D, the motor is accelerated just before and through the transition to provide the volume of flow that compensates for the relatively short period of time (compared to FIGS. 9A-9C) when the pump output is below the nominal flow rate. Uniphasic compensation with compensation before the reversal as in FIG. 9A or with compensation after the reversal as in FIG. 9B may also be used with motor independent reversing mechanisms.

Figure 9E:
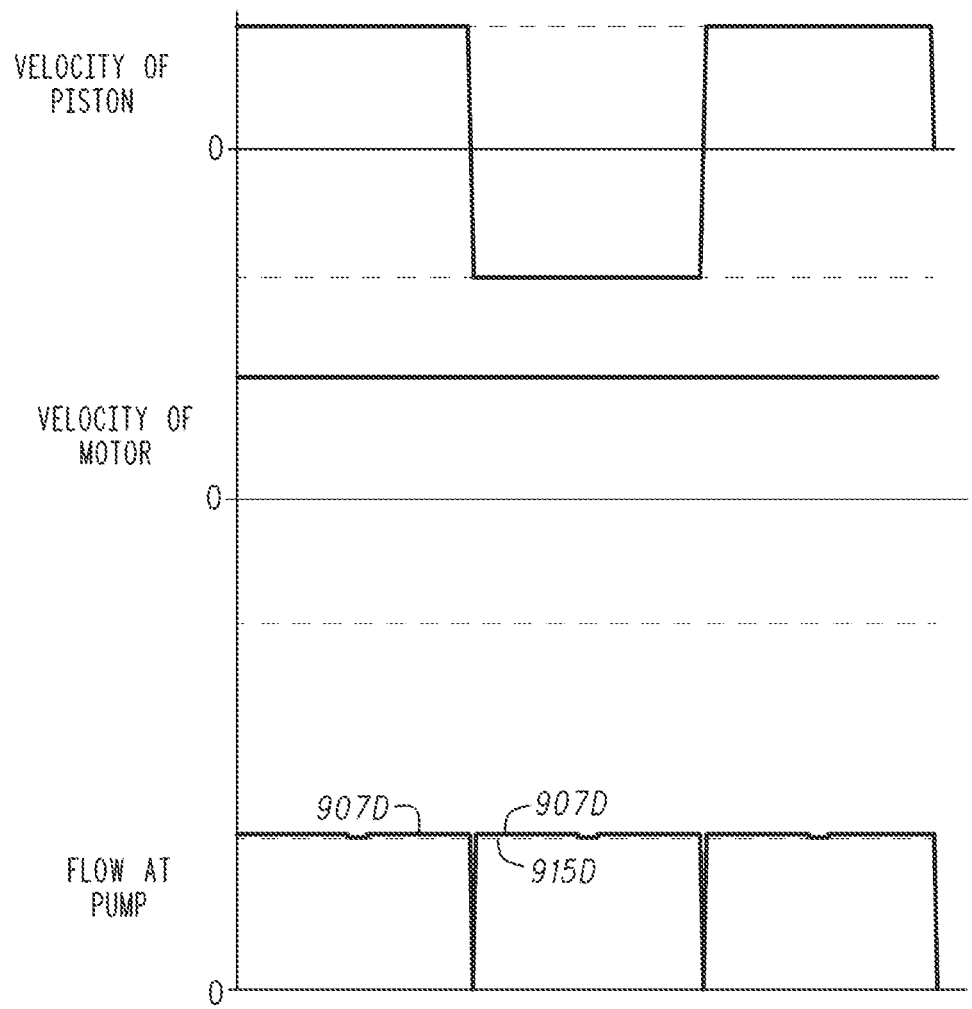
FIG. 9E is a composite velocity and flow plot using another example of a control algorithm for a double action infusion pump having a motor operating substantially continuously and at a substantially continuous velocity.

FIG. 9E shows an alternative embodiment in which the motor operates continuously or almost continuously at a velocity and thus flow rate 907D which is slightly above the nominal flow rate shown as dotted line 915D so that the volume lost during the transition is made up over the whole cycle or a significant fraction of a whole cycle (e.g., before and after piston reversal). In another example, this compensation strategy may also be single sided, with compensation just before or just after piston reversal. In selected embodiments, a similar strategy is employed with a motor reversing arrangement. Because the maximum acceleration is limited, the flow deficit is larger and thus may not be damped out sufficiently by the downstream fluid path element or elements, such as for example catheter 110

In another embodiment a motor independent reversing means is used with a pump that pumps different volumes in the forward and reverse direction for the same displacement. Thus the motor changes speed between the forward stroke and the reverse stroke, but because the change in velocity is much less that in the embodiments in which the motor switches direction, the flow deficit is similarly less. In this situation, the algorithm uses any of the 3 compensation schemes shown in FIGS. 9A, 9B, and 9C where the compensation takes place before, after, or both before and after the transition, respectively.

Various Notes & Examples

Example 1 can include subject matter such as an infusion system comprising: a double action infusion pump configured to deliver a flow of fluid, the double action infusion pump includes: a cylinder having a cylinder interior, a reciprocating piston received within the cylinder, the reciprocating piston separating a first pump chamber from a second pump chamber of the cylinder, and first and second fluid outlets in communication with the first and second pump chambers, respectively, the first and second fluid outlets on a side of the cylinder; and an outlet orientation carriage coupled with the cylinder, the fluid outlets are movable between an operating configuration and purging configuration with the outlet orientation carriage: in the purging configuration the fluid outlets are directed in an upward direction relative to the cylinder interior, and in the operating configuration the fluid outlets are directed away from the upward direction.

Example 2 can include, or can optionally be combined with the subject matter of Example 1, to optionally include wherein the outlet orientation carriage includes a cradle sized and shaped to receive the cylinder: in the purging configuration the cylinder is rotated relative to the cradle with the fluid outlets directed in the upward direction, and in the operating configuration the cylinder is rotated relative to the cradle with the fluid outlets directed away from the upward direction.

Example 3 can include, or can optionally be combined with the subject matter of one or any combination of Examples 1 or 2 to optionally include wherein the cradle has an inner shape corresponding to an outer shape of the cylinder, the inner shape received within the outer shape.

Example 4 can include, or can optionally be combined with the subject matter of one or any combination of Examples 1-3 to optionally include wherein the cylinder is rotatably coupled to the outlet orientation carriage with cylinder joints interposed between the cylinder and the outlet orientation carriage: in the purging configuration the cylinder is rotated relative to the outlet orientation carriage with the fluid outlets directed in the upward direction, and in the operating configuration the cylinder is rotated relative to the outlet orientation carriage with the fluid outlets directed away from the upward direction.

Example 5 can include, or can optionally be combined with the subject matter of one or any combination of Examples 1-4 to optionally include a system base, the outlet orientation carriage rotatably coupled to the system base with carriage joints: in the purging configuration the outlet orientation carriage and the cylinder are rotated relative to the system base with the fluid outlets directed in the upward direction, and in the operating configuration the outlet orientation carriage and the cylinder are rotated relative to the system base with the fluid outlets directed away from the upward direction.

Example 6 can include, or can optionally be combined with the subject matter of Examples 1-5 to optionally include a drive mechanism coupled with the reciprocating piston, the drive mechanism configured to rotate in at least a first rotational direction; and a reversing mechanism coupled between the drive mechanism and the reciprocating piston, wherein the reciprocating piston is moved in opposing first and second directions with the reversing mechanism and rotation of the drive mechanism in the first rotational direction: the piston moves in the first direction with rotation of the drive mechanism in the first rotation direction and the reversing mechanism in a first configuration, and the piston moves in the second direction with rotation of the drive mechanism in the first rotation direction and the reversing mechanism in a second configuration.

Example 7 can include, or can optionally be combined with the subject matter of Examples 1-6 to optionally include wherein the reversing mechanism includes at least one of a ball reverser actuator having a cage coupled with the piston and a cross grooved shaft coupled with the drive mechanism.

Example 8 can include, or can optionally be combined with the subject matter of Examples 1-7 to optionally include wherein the reversing mechanism includes a rolling ring drive coupled with a shaft, the shaft coupled with the drive mechanism.

Example 9 can include, or can optionally be combined with the subject matter of Examples 1-8 to optionally include wherein a fluid source is coupled with the first and second pump chambers with first and second fluid inlets, respectively, and a catheter is coupled with the first and second pump chambers with first and second fluid outlets, respectively.

Example 10 can include, or can optionally be combined with the subject matter of Examples 1-9 to optionally include wherein the reciprocating piston is reciprocated along an intermediate segment of the cylinder and through top and bottom zones, and along the intermediate segment of the cylinder the reciprocating piston moves at a first piston speed, and within the top and bottom zones the reciprocating piston moves at a second piston speed greater than the first piston speed.

Example 11 can include, or can optionally be combined with the subject matter of Examples 1-10 to optionally include wherein a drive mechanism moves the reciprocating piston at least at the first and second piston speeds to provide continuous output of fluid at a catheter.

Example 12 can include, or can optionally be combined with the subject matter of Examples 1-11 to optionally include wherein the second piston speed includes a plurality of speeds including an initial piston speed and a terminating piston speed, and an initial piston speed near an interface of each of the top and bottom zones within the intermediate segment is greater than the first piston speed in the intermediate segment, and a terminating piston speed near ends of the top and bottom zones is greater than the initial piston speed.

Example 13 can include, or can optionally be combined with the subject matter of Examples 1-12 to optionally include wherein the double action infusion pump includes a piston shaft coupled with the reciprocating piston, the piston shaft extends through the first and second pump chambers, the first and second pump chambers having the same flow rate with reciprocation of the reciprocating piston.

Example 14 can include, or can optionally be combined with the subject matter of Examples 1-13 to optionally include a method of using an infusion system comprising: coupling first and second inlets of a double action infusion pump with a fluid source, the double action infusion pump including a cylinder and a reciprocating piston received in the cylinder; purging gas from first and second pump chambers of the cylinder, purging including: orienting first and second outlets of the double action infusion pump in an upward direction relative to a cylinder interior, and pumping fluid from each of the first and second inlets, through the first and second pump chambers and through the first and second outlets, pumping carrying gas in the cylinder out through the first and second outlets in the upward direction; and orienting the first and second outlets of the double action infusion pump in a direction away from the upward direction.

Example 15 can include, or can optionally be combined with the subject matter of Examples 1-14 to optionally include wherein orienting the first and second outlets includes orienting the cylinder and the first and second outlets with an outlet orientation carriage coupled with the cylinder.

Example 16 can include, or can optionally be combined with the subject matter of Examples 1-15 to optionally include wherein orienting with the outlet orientation carriage includes rotating the cylinder at rotatable joints coupling the cylinder with the outlet orientation carriage.

Example 17 can include, or can optionally be combined with the subject matter of Examples 1-16 to optionally include wherein orienting with the outlet orientation carriage includes rotating the outlet orientation carriage at carriage joints and correspondingly rotating the cylinder and the first and second outlets.

Example 18 can include, or can optionally be combined with the subject matter of Examples 1-17 to optionally include injecting a contrast fluid, injecting including: pumping fluid from each of the first and second inlets, through the first and second pump chambers and through the first and second outlets directed away from the upward direction, and retaining incidental gas near apexes of the first and second pump chambers according to orienting of the first and second outlets in the direction way from the upward direction.

Example 19 can include, or can optionally be combined with the subject matter of Examples 1-18 to optionally include wherein pumping fluid includes varying the speed of the reciprocating piston between an intermediate segment of the cylinder and within top and bottom zones of the cylinder including: moving the reciprocating piston at a first piston speed along the intermediate segment, and moving the reciprocating piston at a second piston speed greater than the first piston speed within the top and bottom zones.

Example 20 can include, or can optionally be combined with the subject matter of Examples 1-19 to optionally include wherein moving the reciprocating piston at the second piston speed includes: moving the reciprocating piston near an interface between the intermediate segment and each of the top and bottom zones includes moving at an initial piston speed greater than the first piston speed in the intermediate segment, and moving the reciprocating piston near ends of the top and bottom zones includes moving at a terminating piston speed greater than the initial piston speed.

Example 21 can include, or can optionally be combined with the subject matter of Examples 1-20 to optionally include an infusion system comprising: a double action infusion pump configured to deliver a flow of fluid, the double action infusion pump includes: a cylinder having a cylinder interior extending from a first end to a second end, and a piston shaft extending through the cylinder interior and the first and second ends, the piston shaft including a reciprocating piston between the first and second ends; a drive mechanism coupled with the piston shaft, the drive mechanism configured to rotate in at least a first rotational direction; and a reversing mechanism coupled between the drive mechanism and the piston shaft, wherein the reciprocating piston is moved in opposing first and second directions with the reversing mechanism and rotation of the drive mechanism in the first rotational direction: the piston moves in the first direction with rotation of the drive mechanism in the first rotation direction and the reversing mechanism in a first configuration, and the piston moves in the second direction with rotation of the drive mechanism in the first rotation direction and the reversing mechanism in a second configuration.

Example 22 can include, or can optionally be combined with the subject matter of Examples 1-21 to optionally include wherein the reversing mechanism includes a piston shaft carriage, the first and second ends of the piston shaft coupled with first and second end portions of the piston shaft carriage.

Example 23 can include, or can optionally be combined with the subject matter of Examples 1-22 to optionally include wherein the reversing mechanism includes a ball reverser actuator having a cage coupled with the piston shaft carriage and a cross grooved shaft coupled with the drive mechanism.

Example 24 can include, or can optionally be combined with the subject matter of Examples 1-23 to optionally include wherein in the first configuration balls of the cage are within a first groove track of the cross groove shaft, and in the second configuration balls of the cage are within a second groove track of the cross groove shaft.

Example 25 can include, or can optionally be combined with the subject matter of Examples 1-24 to optionally include wherein the reversing mechanism includes a rolling ring drive coupled between the piston shaft carriage and a shaft.

Example 26 can include, or can optionally be combined with the subject matter of Examples 1-25 to optionally include wherein in the first configuration a rolling ring of the rolling ring drive is tilted at a first angle, and in the second configuration the rolling ring is tilted at a second angle different from the first angle.

Example 27 can include, or can optionally be combined with the subject matter of Examples 1-26 to optionally include wherein one or more of the drive mechanism or the reversing mechanism changes the speed of the piston near the first and second ends relative to an intermediate portion of the cylinder interior.

Example 28 can include, or can optionally be combined with the subject matter of Examples 1-27 to optionally include wherein the piston is reciprocated along an intermediate segment and through top and bottom zones of the cylinder interior: along the intermediate segment the drive mechanism rotates in the first rotation direction at a first rotational speed and the piston moves at a first piston speed, and within the top and bottom zones the drive mechanism rotates in the first rotation direction at a second rotational speed greater than the first rotational speed and the piston moves at a second piston speed greater than the first piston speed.

Example 29 can include, or can optionally be combined with the subject matter of Examples 1-28 to optionally include wherein the piston is reciprocated along an intermediate segment and through top and bottom zones of the cylinder interior: along the intermediate segment the drive mechanism rotates in the first rotation direction at a rotational speed and the reversing mechanism moves the reciprocating piston at a first piston speed, and within the top and bottom zones the drive mechanism rotates in the first rotation direction at the rotational speed and the reversing mechanism moves the reciprocating piston at a second piston speed greater than the first piston speed.

Example 30 can include, or can optionally be combined with the subject matter of Examples 1-29 to optionally include wherein the reversing mechanism includes a ball reverser actuator having a cage coupled with the piston shaft and a cross grooved shaft coupled with the drive mechanism: the cage, piston and piston shaft move at the first piston speed within the intermediate segment with one or more of first or second groove tracks of the cross grooved shaft having a first pitch portion, and the cage, piston and piston shaft move at the second piston speed within the top and bottom zones with one or more of the first or second groove tracks having a second pitch portion having a greater pitch and the first pitch portion.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An infusion system comprising:
 a double action infusion pump including:
  a cylinder having a cylinder interior,
  a reciprocating piston received within the cylinder, the reciprocating piston separating a first pump chamber from a second pump chamber of the cylinder, and
  a first fluid outlet and a second fluid outlet in communication with the first and second pump chambers, respectively, the first and second fluid outlets on a side of the cylinder; and
 an outlet orientation carriage coupled with the cylinder, the outlet orientation carriage configured to rotate the cylinder around a horizontal axis of the cylinder, wherein the first and second fluid outlets are movable between an operating configuration and a purging configuration with rotation of the cylinder, such that:
  in the purging configuration, the first and second fluid outlets are directed in an upward direction relative to the cylinder interior at an apex of the cylinder interior and uniformly spaced from the horizontal axis, and
  in the operating configuration, the first and second fluid outlets are directed away from the upward direction and remote from the apex of the cylinder interior.

2. The infusion system of claim 1, wherein the outlet orientation carriage includes a cradle sized and shaped to receive the cylinder, such that:
 in the purging configuration, the cylinder is rotated relative to the cradle with the fluid outlets directed in the upward direction, and
 in the operating configuration, the cylinder is rotated relative to the cradle with the fluid outlets directed away from the upward direction.

3. The infusion system of claim 2, wherein the cradle has an inner shape corresponding to an outer shape of the cylinder, the outer shape received within the inner shape.

4. The infusion system of claim 1, wherein the cylinder is rotatably coupled to the outlet orientation carriage with cylinder joints interposed between the cylinder and the outlet orientation carriage, such that:
 in the purging configuration, the cylinder is rotated relative to the outlet orientation carriage with the fluid outlets directed in the upward direction, and
 in the operating configuration, the cylinder is rotated relative to the outlet orientation carriage with the fluid outlets directed away from the upward direction.

5. The infusion system of claim 1 comprising a system base, the outlet orientation carriage rotatably coupled to the system base with carriage joints, such that:
 in the purging configuration, the outlet orientation carriage and the cylinder are rotated relative to the system base with the fluid outlets directed in the upward direction, and
 in the operating configuration, the outlet orientation carriage and the cylinder are rotated relative to the system base with the fluid outlets directed away from the upward direction.

6. The infusion system of claim 1 comprising:
 a drive mechanism coupled with the reciprocating piston, the drive mechanism configured to rotate in at least a first rotational direction; and
 a reversing mechanism coupled between the drive mechanism and the reciprocating piston, wherein the reciprocating piston is moved in opposing first and second directions with the reversing mechanism and rotation of the drive mechanism in the first rotational direction, such that:
  the reciprocating piston moves in the first direction with rotation of the drive mechanism in the first rotation direction and the reversing mechanism in a first configuration, and
  the reciprocating piston moves in the second direction with rotation of the drive mechanism in the first rotation direction and the reversing mechanism in a second configuration.

7. The infusion system of claim 6, wherein the reversing mechanism includes at least one of a ball reverser actuator having a cage coupled with the reciprocating piston and a cross grooved shaft coupled with the drive mechanism.

8. The infusion system of claim 6, wherein the reversing mechanism includes a rolling ring drive coupled with a shaft, the shaft coupled with the drive mechanism.

9. The infusion system of claim 1, wherein
a fluid source is coupled with the first and second pump chambers with first and second fluid inlets, respectively, and
a catheter is coupled with the first and second pump chambers with first and second fluid outlets, respectively.

10. The infusion system of claim 1, wherein the reciprocating piston is reciprocated along an intermediate segment of the cylinder and through top and bottom zones, wherein:
along the intermediate segment of the cylinder the reciprocating piston moves at a first piston speed, and
within the top and bottom zones the reciprocating piston moves at a second piston speed greater than the first piston speed.

11. The infusion system of claim 10, wherein a drive mechanism moves the reciprocating piston at least at the first and second piston speeds to provide continuous output of fluid at a catheter.

12. The infusion system of claim 10, wherein the second piston speed includes a plurality of speeds including an initial piston speed and a terminating piston speed, wherein:
the initial piston speed near an interface of each of the top and bottom zones within the intermediate segment is greater than the first piston speed in the intermediate segment, and
the terminating piston speed near ends of the top and bottom zones is greater than the initial piston speed.

13. The infusion system of claim 1, wherein the double action infusion pump includes a piston shaft coupled with the reciprocating piston, the piston shaft extends through the first and second pump chambers, the first and second pump chambers having the same flow rate with reciprocation of the reciprocating piston.

14. A method of using an infusion system, the method comprising: coupling first and second inlets of a double action infusion pump with a fluid source, the double action infusion pump including a cylinder and a reciprocating piston received in the cylinder;
purging gas from first and second pump chambers of the cylinder with an outlet orientation carriage coupled with the cylinder, purging including:
orienting first and second outlets of the double action infusion pump in an upward direction at an apex of a cylinder interior in a purging configuration, wherein orienting includes rotating the cylinder around a horizontal axis of the cylinder with the outlet orientation carriage, and the first and second outlets are uniformly spaced from the horizontal axis of the cylinder, and pumping fluid from each of the first and second inlets, through the first and second pump chambers, and through the first and second outlets at the apex of the cylinder interior, pumping carrying gas in the cylinder out through the first and second outlets in the upward direction; and
orienting the first and second outlets of the double action infusion pump away from the upward direction and the apex of the cylinder interior in an operating configuration.

15. The method of claim 14, wherein orienting with the outlet orientation carriage includes rotating the cylinder at rotatable joints coupling the cylinder with the outlet orientation carriage.

16. The method of claim 14, wherein orienting with the outlet orientation carriage includes rotating the outlet orientation carriage at carriage joints and correspondingly rotating the cylinder and the first and second outlets.

17. The method of claim 14 comprising injecting a contrast fluid, injecting including:
pumping fluid from each of the first and second inlets, through the first and second pump chambers and through the first and second outlets directed away from the upward direction, and
retaining incidental gas near apexes of the first and second pump chambers according to orienting of the first and second outlets in the direction away from the upward direction.

18. The method of claim 17, wherein pumping fluid includes varying a speed of the reciprocating piston between an intermediate segment of the cylinder and within top and bottom zones of the cylinder including:
moving the reciprocating piston at a first piston speed along the intermediate segment, and
moving the reciprocating piston at a second piston speed greater than the first piston speed within the top and bottom zones.

19. The method of claim 18, wherein moving the reciprocating piston at the second piston speed includes:
moving the reciprocating piston near an interface between the intermediate segment and each of the top and bottom zones, and includes moving at an initial piston speed greater than the first piston speed in the intermediate segment, and
moving the reciprocating piston near ends of the top and bottom zones, and includes moving at a terminating piston speed greater than the initial piston speed.

* * * * *